(12) United States Patent
Yeung, Jr. et al.

(10) Patent No.: US 10,877,045 B2
(45) Date of Patent: Dec. 29, 2020

(54) COMPOSITIONS AND METHODS FOR DIAGNOSING AND TREATING ENDOMETRIOSIS-RELATED INFERTILITY

(71) Applicant: Saint Louis University, St. Louis, MO (US)

(72) Inventors: Patrick Yeung, Jr., Sunset Hills, MO (US); Daniela Salvemini, Chesterfield, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/745,920

(22) PCT Filed: Jul. 20, 2016

(86) PCT No.: PCT/US2016/043081
§ 371 (c)(1),
(2) Date: Jan. 18, 2018

(87) PCT Pub. No.: WO2017/015334
PCT Pub. Date: Jan. 26, 2017

(65) Prior Publication Data
US 2018/0217154 A1 Aug. 2, 2018

Related U.S. Application Data

(60) Provisional application No. 62/194,959, filed on Jul. 21, 2015.

(51) Int. Cl.
*G01N 33/68* (2006.01)
*C12Q 1/6883* (2018.01)

(52) U.S. Cl.
CPC ......... *G01N 33/689* (2013.01); *C12Q 1/6883* (2013.01); *C12Q 2600/158* (2013.01); *G01N 2333/726* (2013.01); *G01N 2333/91215* (2013.01); *G01N 2800/364* (2013.01); *G01N 2800/52* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,777,127 A | 10/1988 | Suni et al. |
| 4,816,567 A | 3/1989 | Cabilly et al. |
| 5,137,919 A | 8/1992 | Igarashi et al. |
| 5,151,360 A | 9/1992 | Handa et al. |
| 5,219,740 A | 6/1993 | Miller et al. |
| 5,248,824 A | 9/1993 | Igarashi et al. |
| 5,260,288 A | 11/1993 | Igarashi et al. |
| 5,331,014 A | 7/1994 | Kimura et al. |
| 5,391,800 A | 2/1995 | Igarashi et al. |
| 5,422,120 A | 6/1995 | Kim et al. |
| 5,466,716 A | 11/1995 | Igarashi et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,580,717 A | 12/1996 | Dower et al. |
| 5,580,859 A | 12/1996 | Felgner et al. |
| 5,585,089 A | 12/1996 | Queen et al. |
| 5,625,126 A | 4/1997 | Lonberg et al. |
| 5,627,171 A | 5/1997 | Park et al. |
| 5,633,425 A | 5/1997 | Lonberg et al. |
| 5,661,016 A | 8/1997 | Lonberg et al. |
| 5,693,761 A | 12/1997 | Queen et al. |
| 5,693,762 A | 12/1997 | Queen et al. |
| 5,733,743 A | 3/1998 | Johnson et al. |
| 5,747,014 A | 5/1998 | Cauwet et al. |
| 5,750,373 A | 5/1998 | Garrard et al. |
| 5,807,715 A | 9/1998 | Morrison et al. |
| 5,814,482 A | 9/1998 | Dubensky, Jr. et al. |
| 5,866,692 A | 2/1999 | Shitara et al. |
| 5,997,867 A | 12/1999 | Waldmann et al. |
| 6,054,297 A | 4/2000 | Carter et al. |
| 6,121,230 A * | 9/2000 | Charnock-Jones .... A61K 31/00 424/134.1 |
| 6,180,370 B1 | 1/2001 | Queen et al. |
| 6,180,377 B1 | 1/2001 | Morgan et al. |
| 6,210,671 B1 | 4/2001 | Co |
| 6,265,150 B1 | 7/2001 | Terstappen et al. |

(Continued)

FOREIGN PATENT DOCUMENTS

| | | |
|---|---|---|
| EP | 0345242 A2 | 12/1989 |
| EP | 0519596 A1 | 12/1992 |

(Continued)

OTHER PUBLICATIONS

Markus Gräler, Cell Physiol Biochem 2010; 26:79-86 (Year: 2010).*
Sanllehí et al., Chemistry and Physics of Lipids, 2016; 197: 69-81 (Year: 2016).*
Johnson et al., JBC, 2003; 278: 34521-34547 (Year: 2003).*
Gaetje et al., Geburtsh Frauenheilk 2009; 69: 935-939 (Year: 2009).*
Pirollo et al., Cancer Res. 2008; 68: 1247-1250 (Year: 2008).*
Winkler, Ther. Deliv. 2013; 4: 791-809 (Year: 2013).*
Jafarlou et al., Journal of Biological Regulators & Homeostatic Agents, 2016: 30: 315-321 (Year: 2016).*
Greaves et al., The American Journal of Pathology, 2014; 184: 1930-1939 (Year: 2014).*

(Continued)

*Primary Examiner* — Christina M Borgeest
(74) *Attorney, Agent, or Firm* — Stinson LLP

(57) ABSTRACT

Disclosed are methods of diagnosing and treating endometriosis, and in particular, endometriosis-associated infertility.

11 Claims, 1 Drawing Sheet

(56) References Cited

U.S. PATENT DOCUMENTS

| | | | |
|---|---|---|---|
| 6,331,415 B1 | 12/2001 | Cabilly et al. | |
| 6,350,861 B1 | 2/2002 | Co | |
| 6,753,423 B1 | 6/2004 | Cook et al. | |
| 6,858,383 B2 | 2/2005 | Sabbadini | |
| 6,881,546 B2 | 4/2005 | Sabbadini | |
| 7,172,879 B2 | 2/2007 | Gamble et al. | |
| 7,829,674 B2 | 11/2010 | Sabbadini et al. | |
| 2010/0098700 A1* | 4/2010 | Sabbadini | A61K 39/39591 424/141.1 |

FOREIGN PATENT DOCUMENTS

| | | | |
|---|---|---|---|
| EP | 0524968 B1 | 7/1995 | |
| GB | 2200651 A | 8/1988 | |
| WO | 199007936 A1 | 7/1990 | |
| WO | 199011092 A1 | 10/1990 | |
| WO | 199102805 A1 | 3/1991 | |
| WO | 199114445 A1 | 10/1991 | |
| WO | 199303769 A1 | 3/1993 | |
| WO | 199310218 A1 | 5/1993 | |
| WO | 199311230 A1 | 6/1993 | |
| WO | 199319191 A1 | 9/1993 | |
| WO | 199325234 A1 | 12/1993 | |
| WO | 199325698 A1 | 12/1993 | |
| WO | 199403622 A1 | 2/1994 | |
| WO | 199412649 A1 | 6/1994 | |
| WO | 199423697 A1 | 10/1994 | |
| WO | 199428938 A1 | 12/1994 | |
| WO | 199500655 A1 | 1/1995 | |
| WO | 199507994 A1 | 3/1995 | |
| WO | 199511984 A1 | 5/1995 | |
| WO | 199513796 A1 | 5/1995 | |
| WO | 199530763 A1 | 11/1995 | |
| WO | 199617072 A3 | 6/1996 | |
| WO | 199742338 A1 | 11/1997 | |
| WO | 199806048 A2 | 2/1998 | |
| WO | 199912533 A1 | 3/1999 | |
| WO | 199958572 A1 | 11/1999 | |
| WO | 200127160 A1 | 4/2001 | |
| WO | WO 2006/078336 * | 7/2006 | A61K 39/395 |
| WO | 2008070344 A2 | 6/2008 | |
| WO | WO 2009/124294 * | 10/2009 | A61K 39/395 |
| WO | WO 2010/065491 * | 6/2010 | A61K 31/203 |

OTHER PUBLICATIONS

Bernardi and Pavone, Women's Health, 2013; 9: 233-250 (Year: 2013).*
Andrea Huwiler and Josef Pfeilschifter, Biochemical Pharmacology, 2008; 75: 1893-1900 (Year: 2008).*
Laudanski et al., European Journal of Obstetrics & Gynecology and Reproductive Biology, 2014; 172: 85-92 (Year: 2014).*
Irungu et al., Clin Proteom, 2019; 16:14 (Year: 2019).*
Martin et al., Expert Opin. Investig. Drugs, 2007; 16: 505-518 (Year: 2007).*
Fadhlaoui et al., Frontiers in Surgery, Jul. 2014, vol. 1; doi: 10.3389/fsurg.2014.00024 (Year: 2014).*
Harris & Tsaltas Jul. 2017, Journal of Endometriosis and Pelvic Pain Disorders vol. 9, Issue 3; https://doi.org/10.5301/jeppd.5000296 (Year: 2017).*
Aznaurova et al., Molecular aspects of development and regulation of endometriosis; reproductive biology and endocrinology, 2014, vol. 12, No. 50, 25-pages.
Ballard et al., Can specific pain symptoms help in the diagnosis of endometriosis? A cohort study of women with thronic pelvic pain; Fertility and Sterility, 2010, vol. 94, No. 1, 20-pages.
Boerner et al., Production of Antigen-Specific Human Monoclonal Antibodies From In Vitro-Primed Human Splenocytes; The Journal of Immunology; 1991, vol. 147, No. 1, pp. 86-95.
Brinkmann et al., Fingolimod (FTY720): discovery and development of an oral drug to treat multiple sclerosis; Nature Reviews/Drug Discovery; 2010, vol. 9, pp. 383-397.
Brosens et al., Endometriosis in adolescents is a hidden, progressive and sever disease that deserves attention, not just compassion; Human Reproduction; 2013, vol. 28, No. 8, pp. 2026-2031.
Brown et al., Tumor-specific Genetically Engineered Murine/Human Chimeric Monoclonal Antibody; Cancer Research, 1987, vol. 47, pp. 3577-3583.
Bryant et al., Spinal ceramide and neuronal apoptosis in morphine antinocipeptive tolerance; Neuroscience Letters, 2009, vol. 463, pp. 49-53.
Chomczynski et al., Single-Step Method of RNA Isolation by Acid Guanidinium Thiocyanate-Phenol-Chloroform Extraction; Analytical Biochemistry, 1987; vol. 162, pp. 156-159.
Clackson et al., Making antibody fragments using phage display libraries; Letters to Nature; 1991, vol. 352, pp. 624-628.
Connelly et al., In Vivo Gene Delivery and Expression of Physiological Levels of Functional Human Factor VIII in Mice; Human Gene Therapy, 1005, vol. 6, pp. 185-193.
Curiel et al., High-Efficiency Gene Transfer Mediated by Adenovirus Coupled to DNA-Polylysine Complexes; Human gene therapy; 1992; vol. 3, No. 2, pp. 147-154.
Cusack et al., S1P, receptor agonists: Assessment of selectivity and current clinical activity; Current opinion in drug discovery & development; 2010, vol. 13, No. 4, pp. 481-488.
Daugherty et al., Polymerase chain reaction facilitates the cloning, CDR-grafting, and rapid expression of a murine monoclonal antibody directed against the DC18 component of leukocyte integerins; Nucleic Acids Research, 1991, vol. 19, No. 9, 6-pages.
De Jonghe et al., Synthesis and Apoptogenic activity of fluorinated ceramide and dihydroceramide analogues, Bioorg Med Chem Lett. Nov. 1, 1999; 9(21):3159-64.
Delgado et al., Inhibitors of sphingolipid metabolism enzymes; Biochimica Et Biophysica Acta 1758; 2006, pp. 1957-1977.
D'Hooghe et al., Why We Need a Noninvasive Diagnostic Test for Minimal to Mild Endometriosis with a High Sensitivity; Gynecol Obstet Invest; 2006, vol. 62, pp. 136-138.
Doyle et al., Intraplantar-injected ceramide in rats induces hyperalgesia through an NF-kB-and p38 kinase-dependent cyclooxygenase 2/prostaglandin E2 pathway; The FASEB Journal; 2011, 10-pages.
Doyle et al., Sphingosine-1-phosphate acting via the S1P1 receptor is a downstream signaling pathway in ceramide-induced hyperalgesia; Neuroscience Letters; 2011; vol. 499, pp. 4-8.
Fassbender et al., Biomarkers of endometriosis; Gynecological Diseases; 2013, vol. 99, No. 4, 11-pages.
Findeis et al., Targeted delivery of DNA for gene therapy via receptors; Tibtech, 1993, vol. 11, 4-pages.
Giudice et al., Endometriosis; Seminar; Lancet, 2004, vol. 364, pp. 1789-1799.
Griffiths et al., Human anti-self antibodies with high specificity from phage display libraries; The EMBO Journal; 1993, vol. 12, No. 2; pp. 725-734.
Hadfield et al., Delay in the diagnosis of endometriosis: a survey of women from the USA and the UK; Human Reproduction; 1996, vol. 11, No. 4, pp. 878-880.
Hannun et al., Principles of bioactive lipid singalling: lessons from sphingolipids; Nature Reviews/Molecular Cell Biology; 2008; vol. 9, 13-pages.
Hla et al., Sphingosine 1-phosphae (S1P); Neurology, 2011, vol. 76 (Suppl 3); S3-S8.
Hoogenboom et al., By-passing Immunisation Human Antibodies from Synthetic Repertoires of Germline Vh Gene Segements Rearranged in Vitro; J. Mol. Biol. 1002; vol. 227; pp. 381-388, 1992.
Janes et al., The Development and Maintenance of Paclitaxel-induced Neuropathic Pain Require Activation of the Sphingosine 1-Phosphate Receptor Subtype 1*; The Journal of Biological Chemistry; 2014, vol. 289, No. 30, pp. 21082-21097.
Jarrell et al., Consensus Guidelines for the Management of Chronic Pelvic Pain; SOGC Clinical Practice Guidelines; No. 164, Part two fo two, Sep. 2005; 19-pages.
Johnson et al., Human antibody engineering; Current Opinion in Structural Biology, 1993; vol. 3; pp. 564-571.
Jolly, D., Viral vector systems for gene therapy; Cancer Gene Therapy; 1994, vol. 1, No. 1, pp. 51-64.

(56) References Cited

OTHER PUBLICATIONS

Kaplitt et al., Long-term gene expression and phenotypic correction using adeno-assocaited virus vectors in the mammalian brain; Nature Genetics; 1994, vol. 9, 7-pages.

Kennedy et al., Eshire guideline for the diagnosis and treatment of endometriosis; Human Reproduction; 2005, vol. 20, No. 10, pp. 2698-2704.

Kimura et al., Retroviral Delivery of DNA into the Livers of Transgenic Mice Bearing Premalignant and Malignant Hepatocellular Carcinomas; Human Gene Therapy, 1994, vol. 5, pp. 8445-8852.

Kohama et al., Molecular Cloning and Functional Characterization of Murine Sphingosine Kinase*; The Journal of Biological Chemistry; 1998; vol. 273, No. 37; pp. 23722-23728.

Lobuglio et al., Mouse/human chimeric monoclonal antibody in man: Kinetics and immune response; Proc. Natl. Acad. Sci; 1989; vol. 86, pp. 4220-4224.

Lonberg et al., Human Antibodies from Transgenic Mice; Intern. Rev. Immunol. 1995, vol. 13, pp. 65-93.

Mahato et al., Cationic Lipid-Based Gene Delivery Systems: Pharmaceutical Perspectives; Pharmaceutical Research, 1007, vol. 14, No. 7, 7-pages, 1997; pp. 853-859.

Marks et al., By-passing Immunization Human Antibodies from V-gene Libraries Displayed on Phase; J. Mol. Biol. 1991, vol. 222, pp. 581-597.

Marks et al., By-Passing Immunization: Building High Affinity Human Antibodies by Chain Shuffling; Nature Publishing Group, 1009, 5-pages, Biotechnology (NY) Jul. 1992; 10(7):779-83.

McCafferty et al., Phage antibodies: filamentous phage displaying antibody variable domains; Nature, 1990, vol. 348, 3-pages.

Ndengele et al., Spinal Ceramide Modulates the Development of Morphine Antinociceptive Tolerance via Peroxynitrite-Mediated Nitroxidative Stress and Neuroimmune Activation; The Journal of Pharmacology and Experimenatl Therapeutics; 2009, vol. 329-, No. 1, 12-pages.

Peeters et al., Production of antibodies and antibody fragments in plants; Vaccine; 2001, vol. 19, pp. 2756-2761.

Philip et al., Efficient and Sustained Gene Expression in Primary T Lymphocytes and Primary and Cultured Tumor Cells Mediated by Adeno-Associated Virus Plasmid DNA Complexed to Cationic Liposmes; Molecular and Cellular Biology, 1994; vol. 14, No. 4, pp. 2411-2418.

Pollock et al., Transgenic milk as a method for the production of recombinant antibodies; Journal of Immunological Methods; 1999; vol. 231, pp. 147-157.

Riechmann et al., Reshaping human antibodies for therapy; Nature, 1988; vol. 332, No. 24, 5-pages.

Rosen et al., Sphingosine 1-Phosphate and Its Receptors: An Autocrine and Paracrine Network; Nature; 2005, vol. 5, 11-pages.

Rosen et al., Sphingosine 1-Phosphate Receptor Signaling; 2009, 29-pages.

Rosen et al., Modulating tone: the overture of S1P receptor immunotherapeutics; Immunological Reviews, 2008; vol. 223, pp. 221-235, Immunol Rev.

Sabbadini R. A., Sphingosine-1-phosphate antibodies as potential agents in the treatment of cancer and age-related macular degeneration; British Journal of Pharmacology, 2011, vol. 162, pp. 1225-1238.

Salvemini et al., Therapeutic targeting of the ceramide-to-sphingosine 1-phosphate pathway in pain; Trends in Pharmacological Sciences; 2013; vol. 34, No. 2, 9-pages.

Santulli et al., Sphingosine pathway deregulationin endometriotic tissues; Fertility and Sterility; 2012, vol. 97, No. 4, pp. 904-911e-5.

Sevarino et al. Biosynthesis of Thyrotropin-releasing Hormone by a Rat Medullary Thyroid Carcinoma Cell Line*; The Journal of Biological Chemistry; 1988, vol. 263, No. 2, pp. 620-623.

Shaw et al., Characterization of a Mouse/Human Chimeric Monoclonal Antibody (17-1A) to A Colon Cancer Tumor-Associated Antigen; The Journal of Immunology; 1987, vol. 138, pp. 4534-4538.

Sheets et al., Efficient construction of a large nonimmune phage antibody library: The production of high-affinity human single-chain antibodies to protein antigens; Proc. Natl. Acad. Sci; 1999, vol. 95, pp. 6157-6162.

Spiegel et al., The outs and the ins of sphingosine-1-phosphate in immunity; Nature Reviews/Immunology, 2011, vol. 11, pp. 403-415.

Strader et al., Fingolimod (FTY720): A Recently Approved Multiple Sclerosis Drug Based on a Fungal Secondary Metabolite; Journal of Natural Products; ACS Publications, American Chemical Society and American Society of Pharm.; 2011, vol. 74, pp. 900-907.

Stratton et al., Chronic pelvic pain and endometriosis: translational evidence of the relationship and implications; 2011, Human Reproduction Update, vol. 17, No. 3, pp. 327-346.

Taha et al., Sphingosine-1-phosphate receptors: receptor specificity versus functional redundancy; Biochimica et Biophysica Acta 1682; 2004, pp. 48-55.

Vaughan et al., Human Antibodies with Sub-nanomolar Affinities Isolated from a Large Non-immunized Phage Display Library; Nature Biotechnology, 1996, vol. 14, 6-pages.

Verhoeyen et al., Reshaping Human Antibodies: Grafting an Antilysozyme Activity; Science,1988, vol. 239, 4-pages.

Waterhouse et al., Combinatorial infection and in vivo recombination: a strategy for making large phage antibody repertoires; Nucleic Acids Research, 1993, vol. 21, No. 9, pp. 2265-2266.

Winter et al., Man-made antibodies; Nature, 1991, vol. 349, 8-pages.

Winter et al., Making Antibodies by Phage Display Technology; Annu. Rev. Immunol., 1994, vol. 12, pp. 433-455.

Woffendin et al., Nonviral and viral delivery of a human immunodeficiency virus protective gene into primary human T cells; Proc. Natl. Acad. Sci.; 1994; vol. 91, pp. 11581-11585.

Worley et al., Endometriosis-Associated Ovarian Cancer: A Review of Pathogenesis; International Joural of Molecular Sciences; 2013; vol. 14, pp. 5367-5379.

Wu et al., Receptor-mediated Gene Delivery in Vivo; Partial Correction of Genetic Analbuminemia in Niagase Rats*; The Journal of Biological Chemistry, 1991, vol. 266, No. 22, pp. 14338-14342.

Wu et al., Targeting Genes: Delivery and Persistent Exs:pression of a Foreign Gene Driven by Mammalian Regulatory Elements in Vivo*; The Journal of Biological Chemistry; 1989, vol. 264, No. 29, pp. 16985-16987.

Wu et al., Functional Importance of an Sp1- and an NFkB-related Nuclear Protein in a Keratinocyte-specific Promoteorf Rabbit K3 Keratin Gene*; The Journal of Biological Chemistry; 1994; vol. 269, No. 45, pp. 28450-28459.

Yeung et al., Complete laparoscopic excision of endometriosis in teenagers: is postoperative hormonal suppression necessary? Fertility and Sterility, 2011, vol. 95, No. 6, 5-pages.

Zenke et al., Receptor-mediated endocytosis of transferrin-polycation conjugates: An efficient way to introduce DNA into hematopoietic cells; Proc. Natl. Acad. Sci.; 1990, vol. 87, pp. 3655-3659.

\* cited by examiner

COMPOSITIONS AND METHODS FOR DIAGNOSING AND TREATING ENDOMETRIOSIS-RELATED INFERTILITY

This application is a national phase application under 35 U.S.C. § 371 of International Application No. PCT/US2016/043081, filed Jul. 20, 2016, which claims benefit of priority to U.S. Provisional Application Ser. No. 62/194,959, filed Jul. 21, 2015, the entire contents of each of which are hereby incorporated by reference.

BACKGROUND

I. Field

The disclosure relates the fields of medicine, inflammation and reproductive biology. More specifically, it relates to methods of diagnosing endometriosis-related infertility, and methods of treating the same using at least one of sphingosine kinase antagonist, an S1P antagonist, or an S1P receptor antagonist.

II. Related Art

Endometriosis (endometrial tissue normally found in the uterine cavity, found implanted on the peritoneal lining of the pelvis) is a disease that affects an estimated 1 in 10 women of reproductive age (Ciudice & Kao, 2004), with significant impact on their physical, mental, and social well-being. Endometriosis can cause chronic pain and lead to infertility, and has an estimated annual cost in the United States of $18.8-22B (Kennedy et al., 2005). Treatment options for endometriosis-associated pain other than surgery are limited to anti-inflammatories, hormonal suppression and narcotics, and many women continue to have chronic pain after all current medical and surgical therapies have been exhausted (Jarrell et al., 2005). Some have even proposed considering endometriosis-related pain a chronic pain condition (Stratton & Berkley, 2011).

Another critical issue in the management of endometriosis is the ability to diagnose the condition. At present, the only way to diagnose endometriosis is by surgery. There is a delay in diagnosis of endometriosis up to 12 years especially in the adolescent population (Ballard et al., 2010; Hadfield et al., 1996). Endometriosis can be progressive in up to 50% of cases (Brosens et al., 2013). Surgery has been shown to be effective in treating endometriosis-related pain (Jacobson et al., 2001), and optimal excision has been shown to have a low recurrence rate of actual disease in adolescents (Venug et al., 2011). It has also been suggested that that increased expression of S1PR1 in circulating peripheral blood leukocytes (PBLs) may provide a relevant biomarker to predict severity and pain induction outcomes as well as predict patient responses to anti-S1PR1 approaches (Salvemini et al., 2013). The development of a diagnostic test based on peripheral biomarkers has been elusive so far (Fassbender et al., 2013). The identification of a biomarker such as S1PR1 in the blood of patients could lead to the development of an invaluable non-invasive diagnostic test for patients with endometriosis. Such a test would reduce the number of unnecessary diagnostic laparoscopies performed. A non-invasive diagnostic test would be extremely valuable to identify patients who hove endometriosis and who would benefit from surgery (D'Hooghe et al., 2006).

SUMMARY OF THE INVENTION

Thus, the present disclosure provides a method of diagnosing endometriosis in a subject comprising (a) assessing the levels of at least one enzyme that synthesizes or metabolizes sphingosine-1-phosphate and/or the levels of at least one S1P receptor in a subject peripheral blood leukocyte sample; and (b) comparing the levels of at least one enzyme that synthesizes or metabolizes sphingosine-1-phosphate and/or the levels of at least one S1P receptor in said subject sample to a comparable control sample obtained from a healthy subject, wherein elevated levels of at least one enzyme that synthesizes or metabolizes sphingosine-1-phosphate and/or elevated levels of at least one S1P receptor in said subject sample, as compared to said control sample, indicate that said subject has endometriosis.

Assessing may comprise assessing levels of at least one of SPHK1, SPHK2, SGPP1, SGPP2, SGPL1 or SPHKAP. Assessing may comprise assessing levels of at least one S1P receptors. The the S1P receptor may be S1PR1 or S1PR3. Assessing may comprise assessing both the levels of an enzyme that synthesizes or metabolizes sphingosine-1-phosphate and at least one S1P receptor. Assessing may comprise assessing protein levels of said at least one enzyme and/or said at least one receptor. Assessing protein levels may comprise immunologic detection, and mass spectroscopy. Assessing may comprise assessing transcript levels of said at least one enzyme and/or said at least one receptor. Assessing transcript levels may comprise RT-amplification, Northern blotting, and Western blot.

The method may further comprise performing steps (a) and (b) a second time to assess progression of endometriosis. The method may further comprise performing steps (a) and (b) a second time to determine efficacy of an intervening endometriosis treatment. The subject may exhibit one or more symptoms of endometriosis, such as those selected from the group consisting of include pain, diarrhea, dysuria, constipation, chronic fatigue, nausea, vomiting, headaches, low-grade fevers, heavy and/or irregular periods, hypoglycemia or infertility. The subject may not exhibit a symptom of endometriosis. The subject may not be a human or non-human mammal.

A method of treating endometriosis-related infertility in a subject comprising administering to said subject an inhibitor of S1P synthesis or S1P-binding to S1P receptor. The inhibitor may inhibit the expression or activity of at least one of SPHK1, SPHK2, SGPP1, SGPP2, SGPL1, SPHKAP, S1PR$_1$, S1PR$_2$, S1PR$_3$, S1PR$_4$ or S1PR$_5$. The inhibitor may be an antisense oligonucleotide or an inhibitory RNA. The inhibitor may inhibit binding of S1P to an S1P receptor, such as an S1P receptor-binding antibody or an S1P-binding antibody. Treating may reduce one or more symptoms of endometriosis, such as those selected from the group consisting of include pain, diarrhea, dysuria, constipation, chronic fatigue, nausea, vomiting, headaches, low-grade fevers, heavy and/or irregular periods, hypoglycemia or infertility.

The subject may be a human or non-human mammal. Administering may comprise oral, sublingual, transdermal, vaginal, intramuscular or subcutaneous injection. Oral administration may be by pill or tablet, the transdermal administration is by patch, cream, gel or lotion, the vaginal administration is by suppository or gel, and the systemic administration. The method may further comprise repeated administering of said inhibitor time, and/or further comprise administering a second endometriosis-related infertility treatment to said subject, such as hormonal therapy and/or surgical therapy.

The method may further comprising assessing the efficacy of the treatment comprising (a) assessing the levels of at least one enzyme that synthesizes sphingosine-1-phosphate and/or the levels of at least one S1P receptor in a first subject sample containing cells prior to treatment; (b) assessing the levels of the same enzyme or receptor as in step (a) from a second subject sample containing cells after treatment; and (c) comparing the levels of the enzyme or receptor in steps (a) and (b), wherein reduced levels of the least one enzyme that synthesizes sphingosine-1-phosphate and/or reduced levels the at least one S1P receptor in the second subject sample, as compared to the first subject sample, indicates that the treatment is effective.

In yet another embodiment, there is provided a method of diagnosing endometriosis in a subject comprising (a) assessing the levels of sphingosine-1-phosphate in a subject peripheral blood leukocyte sample; and (b) comparing the levels of sphingosine-1-phosphate in said subject sample to a comparable control sample obtained from a healthy subject, wherein elevated levels of sphingosine-1-phosphate in said subject sample, as compared to said control sample, indicate that said subject has endometriosis. The method may further comprising performing steps (a) and (b) a second time to assess progression of endometriosis or to determine efficacy of an intervening endometriosis treatment. The subject may exhibit one or more symptoms of endometriosis, such as pain, diarrhea, dysuria, constipation, chronic fatigue, nausea, vomiting, headaches, low-grade fevers, heavy and/or irregular periods, hypoglycemia or infertility. The subject may not exhibit a symptom of endometriosis. The subject may be a human or non-human mammal.

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The disclosure may be better understood by reference to one or more of these drawings in combination with the detailed description of specific embodiments presented herein FIG. 1—Total $S1PR_1$ expression in the peripheral blood leukocytes from endometriosis sufferers. When compared to patients without endometriosis (control), the level of $S1PR_1$ detected in PBLs elevated in patients positive for endometriosis tended to be greater with the highest level in patients with positive biopsy results. Mean±SEM. The gel image is a representative of all patients tested (n=2-4/group) at 50 µg/well.

DETAILED DESCRIPTION OF THE INVENTION

Figure 1:
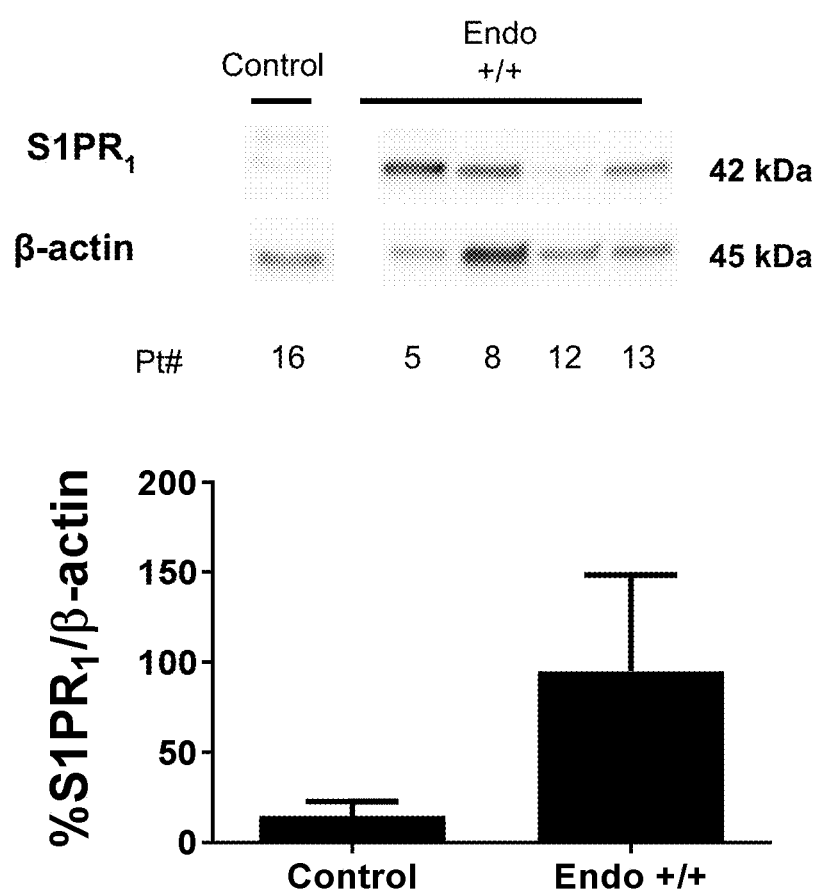

Ceramide, a potent proinflammatory and proapoptotic sphingolipid (Hannun and Obeid, 2008) is generated by enzymatic hydrolysis of sphingomyelin (SM) by sphingomyelinases (SMases) ("SM pathway") and from de novo synthesis by serine palmitoyltransferase (SPT) and ceramide synthase (CS) ("de novo pathway") (Delgado et al., 2006). The development of morphine-induced tolerance is associated with increased formation of ceramide in the spinal cord and inhibition of its biosynthesis blocked the development of antinociceptive tolerance (Bryant et al., 2009; Ndengele et al., 2009). Once generated, the steady-state availability of ceramide is further regulated by ceramidases that convert ceramide to sphingosine (SP), with SP then converted by sphingosine kinase 1 and 2 (Melendez, 2008; Takabe et al., 2008) to sphingosine-1-phosphate (S1P), the GPCR-signaling end product in the ceramide metabolic pathway (Melendez, 2008; Takabe et al., 2008). Once generated, S1P diffuses extracellularly so to act on GPCR-coupled S1P receptors (five identified to date, known respectively as $S1PR_{1-5}$) found on several cells of the CNS including neurons and glial cells (Taha et al., 2004; Melendez, 2008; Takabe et al., 2008).

S1P has potent pro-inflammatory actions which are driven in most part by sphingosine activation of the S1P receptor subtype S1PR1 (Hannun & Obeid, 2008; Rosen & Goetzl, 2005; Rosen et al., 2008; 2009). Biologically active S1P is generated by the phosphorylation of sphingosine, catalyzed by two sphingosine kinases (SphK1, SphK2) (Hannun & Obeid, 2008). S1P levels are further regulated by its dephosphorylation by two phosphatases (SGPP1 and SGPP2) and through degradation by one lyase (SGPL1) (Hannun & Obeid, 2008). Once released, S1P initiates signaling through a family of five cognate 13 protein-coupled receptors ($S1PR_{1-5}$), leading to various cellular responses (Rosen & Geotzl, 2005; Spiegel & Milstien, 2011). S1P signaling has important roles in inflammation and cancer. For example, S1P acting via the SIPR1 has been implicated in the development of pain of several etiologies as discovered by Salvemini and coworkers and subsequently extended by others (Janes et al., 2014; Salvemini et al., 2013). FTY720 (fingolimod/Gilenya®) is the first orally available agent approved by the FDA for the treatment of relapsing-remitting multiple sclerosis (MS) (Brinkman et al., 2010).

The underlying pathogenesis of endometriosis remains largely unknown, but much has been learned about the establishment and progression of the disease which includes local invasion, cell attachment, and proliferation supported by hormonal and immunologic responses, inflammation, and neuroangiogenesis (Aznaurova et al., 2014). A recent study by (Santulli et al. 2012) implicated the contribution of the S1P to S1PR1 axis in the development of endometriosis in humans. In this study, enzymes involved in the biosynthesis of S1P were increased while those involved in its breakdown were decreased in the peritoneal samples of patients with endometriosis. The net effect resulting from such deregulation is expected to be increased S1P signaling. Interestingly, a body of existing literature suggests that endometriosis shares many characteristics with cancer (Worley et al., 2013). Together, these studies suggest that the S1P/S1PR1 axis contributes to the etiology or progression of endometriosis, and therefore may provide a diagnostic tool, particularly in identifying patients with infertility that is linked to endometriosis. Interestingly, S1P blockade contributes a potent anti-tumor agent by inhibiting the strong anti-apoptotic (pro-tumor) effect of S1P (Sabbadini, R. A., 2011). Inhibition of the S1PR1 axis with FTY720 produces anticancer effects, and reduces inflammation.

The work by Salvemini's group, and that reported here, not only provides a mechanistic basis for understanding chronic pain through the S1P/S1PR1 axis, but the opportunity for early new therapeutic intervention with existing agents like FTY720. Anti-S1PR1 approaches, including FTY720, have great potential not just to treat endometriosis-related pain, but as a dual agent against the development or progression of the disease and various symptoms, such as infertility. This work is highly significant as it (1) expands the pioneering work of Salvemini et al. in identifying S1PR1 as a biomarker for predicting response to anti-S1PR1 therapies into the area of endometriosis-related infertility, thus providing another application for therapies such FTY720 (fingolimod/Gilenya®); (2) points to S1P and S1PR as biomarkers for a much-needed non-invasive diagnostic blood test for endometriosis in patients with pain, which has been heretofore elusive; and (3) provides the foundation to explore the signaling pathways engaged by the S1P/S1PR1 axis in endometriosis, and to apply anti-S1P and -S1PR approaches for the treatment of this prevalent condition from which millions of women suffer.

I. Abbreviations and Definitions

To facilitate understanding of the disclosure, a number of terms and abbreviations as used herein are defined below as follows:

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Fv" is an antibody fragment that contains a complete antigen-recognition and binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of an Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy-terminus of the heavy chain CH1 domain including one or more cysteines from the antibody hinge regions.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')2, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited with regard to the source of the antibody or the manner in which it is made (e.g., by hybridoma, phage selection, recombinant expression, transgenic animals, etc.).

As used herein, "human antibody" means an antibody having an amino acid sequence corresponding to that of an antibody produced by a human and has been made using any of the techniques for making human antibodies known in the art. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one aspect, the human antibody is selected from a phage library, where that phage library expresses human antibodies (Vaughan et al., 1996; Sheets et al., 1998; Hoogenboom and Winter, 1991; and Marks et al., 1991). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., 1985; Boerner et al., 1991 and U.S. Pat. No. 5,750,373.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being of human origin, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include Clq binding; complement dependent cytotoxicity (CDC); Fc receptor binding; antibody-dependent cell-mediated cytotoxicity (ADCC); phagocytosis; down-regulation of cell surface receptors (e.g., B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and with an Fc region of a parent polypeptide, and most preferably at least about 90% sequence identity therewith, more preferably at least about 95% sequence identity therewith.

As used herein, the term "LT1009" refers to an antibody generated and characterized in U.S. Pat. No. 7,829,674 and corresponding PCT application PCT/US2007/082647.

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and with greater affinity with a particular cell or substance than it does with alternative cells or substances. An antibody "specifically binds" or "preferentially binds" to a target if it binds with greater affinity, avidity, more readily, and with greater duration than it binds to other substances. For example, an antibody that specifically or preferentially binds to S1P is an antibody that binds this molecule with greater affinity, avidity, more readily, and with greater duration than it binds to other molecules. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, the term "S1P" refers to sphingosine-1-phosphate.

An "S1P receptor," also referred to as "S1PR" refers to a polypeptide that is bound by or activated by S1P. S1P receptors include those of any mammalian species, including, but not limited to, human, canine, feline, equine, primate, or bovine. This definition includes S1P receptor subtypes S1P1, S1P2, S1P3, S1P4 and S1P5, also known as $S1PR_1$, $S1PR_2$, $S1PR_3$, $S1PR_4$, and $S1PR_5$, respectively.

As used herein, an "anti-S1P antibody" refers to an antibody which is able to bind to S1P and inhibit S1P biological activity and downstream pathway(s) mediated by S1P signaling or secondary messenger activity. Anti-S1P antibodies encompass antibodies that block, antagonize, suppress or reduce (including significantly) S1P biological activity, including downstream pathways mediated by S1P signaling, such as receptor binding and elicitation of a cellular response to S1P. For purpose of the present disclosure, it will be explicitly understood that the term "anti-S1P antibody" encompasses all the previously identified terms, titles, and functional states and characteristics whereby the S1P itself, an S1P biological activity (including but not limited to its ability to mediate any aspect of endometriosis), or the consequences of the biological activity, are substantially nullified, decreased, or neutralized in any degree. In some aspects, an anti-S1P antibody binds S1P and prevent S1P dimerization and binding to an S1P receptor, such as S1P1 receptor. In other aspects, an anti-S1P antibody binds S1P and prevents S1P receptor dimerization and S1P phosphorylation. Examples of anti-S1P antibodies include LT1009.

As used herein, an "anti-S1P receptor antibody" refers to an antibody which is able to bind to an S1P receptor and inhibit S1P receptor biological activity. Anti-S1P receptor antibodies encompass antibodies that block, antagonize, suppress or reduce (including significantly) S1P receptor biological activity such as binding and elicitation of a cellular response in conjunction with S1P. For purpose of the present disclosure, it will be explicitly understood that the term "anti-S1P receptor antibody" encompasses all the previously identified terms, titles, and functional states and characteristics whereby the S1P receptor itself, an S1P receptor biological activity (including but not limited to its ability to ability to mediate any aspect of endometriosis), or the consequences of the biological activity, are substantially nullified, decreased, or neutralized in any degree. In some aspects, an anti-S1P receptor antibody binds S1P receptor and prevents S1P dimerization and binding to S1P. In other aspects, an anti-S1P receptor antibody binds an S1P receptor and prevents S1P phosphorylation.

As used herein, "S1P receptor antagonists" include, but are not limited to, anti-S1P antibodies and anti-S1P1 receptor antibodies. They further include small molecule antagonists, including S1P analogs ("functional antagonists") and inhibitory oligonucleotides (antisense, dsRNA, miRNAs, siRNAs).

Reference to "sphingosine kinase" should be understood as a reference to the molecule which is, inter alia, involved in the generation of sphingosine-1-phosphate during the activation of the sphingosine kinase signaling pathway. Methods of detecting sphingosine kinase antagonist activity include those disclosed in U.S. Pat. No. 7,172,879 and in PCT Patent Application No. PCT/AU98/00730 (WO 99/12533), which are incorporated herein by reference in their entirety.

"Biological activity" of S1P generally refers to the ability to bind S1P receptors and activate S1P receptor signaling pathways, including but not limited to S1P1 receptor signaling pathways. Without limitation, a biological activity includes any one or more of the following: the ability to bind an S1P receptor; the ability to promote S1P receptor dimerization and phosphorylation; the ability to activate an S1P receptor signaling pathway; and the ability to mediate endometriosis.

As used herein, "treatment" is an approach for obtaining beneficial or desired clinical results. For purposes of this disclosure, beneficial or desired clinical results include, but are not limited to, one or more of the following: Under the concepts involved in 'treatment', I would include: improving the chances for (clinical pregnancy) and live birth, which are distinct clinical outcomes; reducing the need for repeat surgery; reducing the classification of the endometriosis, based on extent or depth of disease (at present, the accepted classification is the r-ASRM classification); preventing progression of the disease, based on extent or depth of disease; and improving quality of life (using standard measuring tools), including sexual function.

An "effective amount" of drug, compound, or pharmaceutical composition is an amount sufficient to effect beneficial or desired results including clinical results set for the above. An effective amount can be administered in one or more administrations. For purposes of this disclosure, an effective amount of drug, compound, or pharmaceutical composition is an amount sufficient to treat, ameliorate, limit, delay, reduce the intensity of and prevent endometriosis, including symptoms and deficiencies mentioned elsewhere in this document. As is understood in the clinical context, an effective amount of a drug, compound, or pharmaceutical composition may or may not be achieved when administered in conjunction with another drug, compound, or pharmaceutical composition including other currently used compounds such as antidepressants, anticonvulsive, NSAIDs, COX-2 inhibitors, NOS inhibitors and so forth. Thus, an "effective amount" may be considered in the context of administering one or more therapeutic agents, and a single agent may be considered to be given in an effective amount if, in conjunction with one or more other agents, a desirable result may be or is achieved.

"A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. In particular, the sample is a leukocyte-containing sample.

A "subject" is a vertebrate, preferably a mammal, more preferably a human. Mammals include, but are not limited to, farm animals (such as cows), sport animals, pets (such as cats, dogs and horses), primates, mice and rats.

II. Endometriosis

Endometriosis is a disease whose pathophysiology is not well understood. There are hormonal and immunologic components to the disease, but there are epiphenomena as well including inflammation, increase in anti-oxidants, neoangiogenesis, immune deficiency and possibly stem cell effects. In endometriosis, cells similar to that which line the uterus (endometrium) grow outside the uterine cavity, most commonly on the membrane which lines the abdominal cavity, the peritoneum. The uterine cavity is lined with endometrial cells, which are under the influence of female hormones. Endometrial cells in areas outside the uterus are also influenced by hormonal changes and respond in a way that is similar to the cells found inside the uterus. Common symptoms of endometriosis are pain and infertility.

The pain often is worse with the menstrual cycle and is the most common cause of secondary dysmenorrhea.

Endometriosis is typically diagnosed during the reproductive years, but has been diagnosed in girls as young as 8 and has been found to continue past menopause; it has been estimated that endometriosis occurs in roughly 4-10% of women. Symptoms may depend on the site of active endometriosis. Its main but not universal symptom is pelvic pain in various manifestations. There is a well-established association between endometriosis and infertility. Endometriosis has a significant social and psychological impact. There is no cure for endometriosis, but it can be treated in a variety of ways, including pain medication, hormonal treatments, and surgery.

Current research has demonstrated an association between endometriosis and certain types of cancers, notably some types of ovarian cancer, non-Hodgkin's lymphoma and brain cancer. Despite similarities in their name and location, endometriosis bears no relationship to endometrial cancer. Endometriosis often also coexists with leiomyoma or adenomyosis, but studies that look into similarities and differences between endometriosis and adenomyosis have conflicting results. A 1988 survey conducted in the U.S. found significantly more hypothyroidism, fibromyalgia, chronic fatigue syndrome, autoimmune diseases, allergies and asthma in women with endometriosis compared to the general population.

A. Symptoms

A major symptom of endometriosis is recurring pelvic pain. The pain can range from mild to severe cramping or stabbing pain that occurs on both sides of the pelvis, in the lower back and rectal area, and even down the legs. The amount of pain a woman feels correlates poorly with the extent or stage (1 through 4) of endometriosis, with some women having little or no pain despite having extensive endometriosis or endometriosis with scarring, while other women may have severe pain even though they have only a few small areas of endometriosis. Symptoms of endometriosis-related pain may include:

dysmenorrhea—painful, sometimes disabling cramps during the menstrual period; pain may get worse over time (progressive pain), also lower back pains linked to the pelvis chronic pelvic pain—typically accompanied by lower back pain or abdominal pain dyspareunia—painful sex dysuria—urinary urgency, frequency, and sometimes painful voiding Throbbing, gnawing, and dragging pain to the legs are reported more commonly by women with endometriosis. Compared with women with superficial endometriosis, those with deep disease appear to be more likely to report shooting rectal pain and a sense of their insides being pulled down. Individual pain areas and pain intensity appears to be unrelated to the surgical diagnosis, and the area of pain unrelated to area of endometriosis.

Endometriosis lesions react to hormonal stimulation and may "bleed" at the time of menstruation. The blood accumulates locally, causes swelling, and triggers inflammatory responses with the activation of cytokines. This process may cause pain. Pain can also occur from adhesions (internal scar tissue) binding internal organs to each other, causing organ dislocation. Fallopian tubes, ovaries, the uterus, the bowels, and the bladder can be bound together in ways that are painful on a daily basis, not just during menstrual periods. Also, endometriotic lesions can develop their own nerve supply, thereby creating a direct and two-way interaction between lesions and the central nervous system, potentially producing a variety of individual differences in pain that can, in some women, become independent of the disease itself.

Other symptoms include diarrhea or constipation, chronic fatigue, nausea and vomiting, headaches, low-grade fevers, heavy and/or irregular periods, and hypoglycemia. In addition to pain during menstruation, the pain of endometriosis can occur at other times of the month. There can be pain with ovulation, pain associated with adhesions, pain caused by inflammation in the pelvic cavity, pain during bowel movements and urination, during general bodily movement like exercise, pain from standing or walking, and pain with intercourse. But the most desperate pain is usually with menstruation and many women dread having their periods. Pain can also start a week before a menstrual period, during and even a week after a menstrual period, or it can be constant. The pain can be debilitating and the emotional stress can take a toll.

B. Endometriosis-Related Infertility

The mechanisms by which endometriosis may cause infertility is not clearly understood, particularly when the extent of endometriosis is low. Still possible mechanisms include:

anatomical distortions and adhesions (the fibrous bands that form between tissues and organs following recovery from an injury);

the release of factors from endometriotic cysts which are detrimental to gametes or embryos. An endometriotic cyst contains free iron, reactive oxygen species, proteolytic enzymes and inflammatory molecules. Follicular density in tissue surrounding the endometriotic cyst has been consistently shown to be significantly lower than in healthy ovaries, and to a degree that does not appear to be caused merely by the stretching of surrounding tissues owing to the presence of a cyst.

On the other hand, endometriosis may more likely develop in women who fail to conceive for other reasons and thus be a secondary phenomenon. For this reason it is preferable to speak of "endometriosis-associated infertility" rather than any definite "infertility caused by endometriosis" by the same reason that association does not imply causation.

In younger women with unfulfilled reproductive potential, surgical treatment attempts to remove endometrial tissue and preserving the ovaries without damaging normal tissue. Surgery is more effective for infertility than medicinal intervention in endometriosis. One study has shown that surgical treatment of endometriosis approximately doubles the fecundity (pregnancy rate). The use of medical suppression after surgery for minimal/mild endometriosis has been used in patients with infertility. Use of fertility medication that stimulates ovulation (clomiphene citrate, gonadotropins) combined with intrauterine insemination (IUI) enhances fertility in these patients.

In vitro fertilization (IVF) procedures are effective in improving fertility in many women with endometriosis. IVF makes it possible to combine sperm and eggs in a laboratory and then place the resulting embryos into the woman's uterus. The decision when to apply IVF in endometriosis-associated infertility cases takes into account the age of the patient, the severity of the endometriosis, the presence of other infertility factors, and the results and duration of past treatments. In ovarian hyperstimulation as part of IVF in women with endometriosis, using a standard GnRH agonist protocol has been found to be equally effective in regard to using a GnRH antagonist protocol in terms of pregnancy rate. On the other hand, when using a GnRH agonist protocol, long-term (three to six months) pituitary down-regulation before IVF for women with endometriosis has been estimated to increase the odds of clinical pregnancy by four-fold. It has been shown that cystectomy is superior to incision and drainage for endometriomata for outcomes that matter to patients, including pain, recurrence and fertility. Given that AMH levels (a measure of ovarian reserve) is decreased after cystectomy at 6 months (though some studies show it to rebound at around 1 year), there is a current debate as to whether surgical intervention is needed at all for small endometriomata (which may not affect stimulation protocols, namely <3 cm), in patients undergoing FOR IVF.

C. Complications

Complications of endometriosis include internal scarring, adhesions, pelvic cysts, chocolate cyst of ovaries, ruptured cysts, and bowel and ureteral obstruction resulting from pelvic adhesions or from the disease itself. The disease can affect the quality of life, including sexual function, stress, and mental health among others. Endometriosis-associated infertility, discussed above, can be related to scar formation and anatomical distortions due to the endometriosis. Ovarian endometriosis may complicate pregnancy by decidualization, abscess and/or rupture. Pleural implantations are associated with recurrent right pneumothoraces at times of a menstrual period, termed catamenial pneumothorax.

D. Risk Factors

Genetic predisposition plays a role in endometriosis. Daughters or sisters of women with endometriosis are at higher risk of developing endometriosis themselves; low progesterone levels may be genetic, and may contribute to a hormone imbalance. There is an about 6-fold increased incidence in women with an affected first-degree relative. It has been proposed that endometriosis results from a series of multiple hits within target genes, in a mechanism similar to the development of cancer. In this case, the initial mutation may be either somatic or heritable. Individual genomic changes (found by genotyping including genome-wide association studies) that have been associated with endometriosis include:

Changes on chromosome 1 near WNT4

Changes on chromosome 2 near GREB1

Changes on chromosome 6 near ID4

Changes on chromosome 7 in the 7p15.2 region

Changes on chromosome 9 near CDKN2BAS

Changes on chromosome 10 at region 10q26

Changes on chromosome 12 near VEZT

In addition, there is a weaker association with changes in the fibronectin gene as well as in the 2p14 region of chromosome 2.

In addition, there are many findings of altered gene expression and epigenetics, but both of these can also be a secondary result of, for example, environmental factors and altered metabolism. Examples of altered gene expression include that of miRNAs.

Aging brings with it many effects that may reduce fertility. Depletion over time of ovarian follicles affects menstrual regularity. Endometriosis has more time to produce scarring of the ovary and tubes so they cannot move freely or it can even replace ovarian follicular tissue if ovarian endometriosis persists and grows. Abdominal adhesions from other intraabdominal surgery, or ruptured ovarian cysts can also affect tubal motility needed to sweep the ovary and gather an ovulated follicle (egg). Incidences of endometriosis have occurred in postmenopausal women, and in less common cases, girls may have endometriosis symptoms before they even reach menarche.

E. Pathophysiology

While the exact cause of endometriosis remains unknown, many theories have been presented to better understand and explain its development. These concepts do not necessarily exclude each other. The pathophysiology of endometriosis is likely to be multifactorial and to involve an interplay between several factors.

Broadly, the aspects of the pathophysiology can basically be classified as underlying predisposing factors, inflammation, metabolic changes, formation of ectopic endometrium, and generation of pain and other effects. It is not certain, however, to what degree predisposing factors lead to metabolic and inflammatory changes and so on, or if metabolic and inflammatory changes or formation of ectopic endometrium is the primary cause. Also, there are several theories within each category, but the uncertainty over what is a cause versus what is an effect when considered in relation to other aspects is as true for any individual entry in the pathophysiology of endometriosis. Inflammation is a central part of the etiopathology and causes pain. Also, pathogenic mechanisms appear to differ in the formation of distinct types of endometriotic lesion, such as peritoneal, ovarian and rectovaginal lesions.

The main theories for the formation of ectopic endometrium are retrograde menstruation, müllerianosis, coelomic metaplasia and transplantation, each further described below.

The theory of retrograde menstruation (also called the implantation theory or transplantation theory) is the most widely accepted theory for the formation of ectopic endometrium in endometriosis. It suggests that during a woman's menstrual flow, some of the endometrial debris exits the uterus through the fallopian tubes and attaches itself to the peritoneal surface (the lining of the abdominal cavity) where it can proceed to invade the tissue as endometriosis.

While most women may have some retrograde menstrual flow, typically their immune system is able to clear the debris and prevent implantation and growth of cells from this occurrence. However, in some women, endometrial tissue transplanted by retrograde menstruation may be able to implant and establish itself as endometriosis. Factors that might cause the tissue to grow in some women but not in others need to be studied, and some of the possible causes below may provide some explanation, e.g., hereditary factors, toxins, or a compromised immune system. It can be argued that the uninterrupted occurrence of regular menstruation month after month for decades is a modern phenomenon, as in the past women had more frequent menstrual rest due to pregnancy and lactation.

Retrograde menstruation alone is not able to explain all instances of endometriosis, and it needs additional factors such as genetic or immune differences to account for the fact that many women with retrograde menstruation do not have endometriosis. Research is focusing on the possibility that the immune system may not be able to cope with the cyclic onslaught of retrograde menstrual fluid. In this context there is interest in studying the relationship of endometriosis to autoimmune disease, allergic reactions, and the impact of toxins. It is still unclear what, if any, causal relationship exists between toxins, autoimmune disease, and endometriosis. There are immune system changes in women with endometriosis, such as an increase macrophage-derived secretion products, but it is unknown if these are contributing to the disorder or are reactions from it.

In addition, at least one study found that endometriotic lesions are biochemically very different from artificially transplanted ectopic tissue. The latter finding, however, can in turn be explained by that the cells that establish endometrial lesions are not of the main cell type in ordinary endometrium, but rather of a side population cell type, as supported by exhibition of a side population phenotype upon staining with Hoechst dye and by flow cytometry. Similarly, there are changes in for example the mesothelium of the peritoneum in women with endometriosis, such as loss of tight junctions, but it is unknown if these are causes or effects of the disorder.

In rare cases where imperforate hymen does not resolve itself prior to the first menstrual cycle and goes undetected, blood and endometrium are trapped within the uterus of the woman until such time as the problem is resolved by surgical incision. Many health care practitioners never encounter this defect, and due to the flu-like symptoms it is often misdiagnosed or overlooked until multiple menstrual cycles have passed. By the time a correct diagnosis has been made, endometrium and other fluids have filled the uterus and fallopian tubes with results similar to retrograde menstruation resulting in endometriosis. The initial stage of endometriosis may vary based on the time elapsed between onset and surgical procedure.

Other well-known theories include:

Müllerianosis: A competing theory states that cells with the potential to become endometrial are laid down in tracts during embryonic development and organogenesis. These tracts follow the female reproductive (Mullerian) tract as it migrates caudally (downward) at 8-10 weeks of embryonic life. Primitive endometrial cells become dislocated from the migrating uterus and act like seeds or stem cells. This theory is supported by fetal autopsy.

Coelomic metaplasia: This theory is based on the fact that coelomic epithelium is the common ancestor of endometrial and peritoneal cells and hypothesizes that later metaplasia (transformation) from one type of cell to the other is possible, perhaps triggered by inflammation.

Vasculogenesis: Up to 37% of the microvascular endothelium of ectopic endometrial tissue originates from endothelial progenitor cells, which result in de novo formation of microvessels by the process of vasculogenesis rather than the conventional process of angiogenesis.

Neural growth: An increased expression of new nerve fibers is found in endometriosis, but does not fully explain the formation of ectopic endometrial tissue, and is not definitely correlated with the amount of perceived pain.

More modern hypotheses include stem cell involvement and immunological effects.

F. Localization

Most endometriosis is found on these structures in the pelvic cavity: ovaries (the most common site), Fallopian tubes, the back of the uterus and the posterior cul-de-sac, the front of the uterus and the anterior cul-de-sac, uterine ligaments such as the broad or round ligament of the uterus, pelvic and back wall, intestines, most commonly the rectosigmoid, and urinary bladder and ureters Rectovaginal or bowel endometriosis affects approximately 5-12% of women with endometriosis, and can cause severe pain with bowel movements. Endometriosis may spread to the cervix and vagina or to sites of a surgical abdominal incision, known as "scar endometriosis." Risk factors for scar endometriosis include previous abdominal surgeries, such as a hysterectomy or cesarean section, or ectopic pregnancies, salpingostomy puerperal sterilization, laparoscopy, amniocentesis, appendectomy, episiotomy, vaginal hysterectomies, and hernia repair. Endometriosis may also present with skin lesions in cutaneous endometriosis. Less commonly lesions can be found on the diaphragm. Diaphragmatic endometriosis is rare, almost always on the right hemidiaphragm, and may inflict cyclic pain of the right shoulder just before and during a menstrual period. Rarely, endometriosis can be extraperitoneal and is found in the lungs and CNS.

G. Diagnosis

A health history and a physical examination can lead the health care practitioner to suspect endometriosis. Although doctors can often feel the endometrial growths during a pelvic exam, and these symptoms may be signs of endometriosis, diagnosis cannot be confirmed by exam only. Use of pelvic ultrasound may identify large endometriotic cysts (called endometriomas). However, smaller endometriosis implants cannot be visualized with ultrasound technique.

Laparoscopy, a surgical procedure where a camera is used to look inside the abdominal cavity, is the only way to officially diagnose endometriosis as it permits lesion visualization, unless the lesion is visible externally, e.g., an endometriotic nodule in the vagina. If the growths are not visible, a biopsy may be taken to determine the diagnosis. Surgery for diagnoses also allows for surgical treatment of endometriosis at the same time.

To the eye, lesions can appear dark blue, powder-burn black, red, white, yellow, brown or non-pigmented. Lesions vary in size. Some within the pelvis walls may not be visible, as normal-appearing peritoneum of infertile women reveals endometriosis on biopsy in 6-13% of cases. Early endometriosis typically occurs on the surfaces of organs in the pelvic and intra-abdominal areas. Health care providers may call areas of endometriosis by different names, such as implants, lesions, or nodules. Larger lesions may be seen within the ovaries as endometriomas or "chocolate cysts", "chocolate" because they contain a thick brownish fluid, mostly old blood.

Frequently during diagnostic laparoscopy, no lesions are found in women with chronic pelvic pain, a symptom common to other disorders including adenomyosis, pelvic adhesions, pelvic inflammatory disease, congenital anomalies of the reproductive tract, and ovarian or tubal masses.

H. Staging

Surgically, endometriosis can be staged I-IV (Revised Classification of the American Society of Reproductive Medicine). The process is a complex point system that assesses lesions and adhesions in the pelvic organs, but it is important to note staging assesses physical disease only, not the level of pain or infertility. A person with Stage I endometriosis may have little disease and severe pain, while a person with Stage IV endometriosis may have severe disease and no pain or vice versa. In principle the various stages show these findings:

Stage I (Minimal): Findings restricted to only superficial lesions and possibly a few filmy adhesions Stage II (Mild): In addition, some deep lesions are present in the cul-de-sac Stage III (Moderate): As above, plus presence of endometriomas on the ovary and more adhesions.

Stage IV (Severe): As above, plus large endometriomas, extensive adhesions.

Endometrioma on the ovary of any significant size (approx. 2 cm+) must be removed surgically because hormonal treatment alone will not remove the full endometrioma cyst, which can progress to acute pain from the rupturing of the cyst and internal bleeding. Endometrioma is sometimes misdiagnosed as ovarian cysts.

An area of research is the search for endometriosis markers. A systematic review in 2010 of essentially all proposed biomarkers for endometriosis in serum, plasma and urine came to the conclusion that none of them have been clearly shown to be of clinical use, although some appear to be promising. Another review in 2011 identified several putative biomarkers upon biopsy, including findings of small sensory nerve fibers or defectively expressed $\beta 3$ integrin subunit. The one biomarker that has been used in clinical practice over the last 20 years is CA-125. However, its performance in diagnosing endometriosis is low, even though it shows some promise in detecting more severe disease. CA-125 levels appear to fall during endometriosis treatment, but have not shown a correlation with disease response. It has been postulated a future diagnostic tool for endometriosis will consist of a panel of several specific and sensitive biomarkers, including both substance concentrations and genetic predisposition.

I. Management

While there is no cure for endometriosis, there are two types of interventions; treatment of pain and treatment of endometriosis-associated infertility. In many women menopause (natural or surgical) will abate the process. In women in the reproductive years, endometriosis is merely managed: the goal is to provide pain relief, to restrict progression of the process, and to restore or preserve fertility where needed. In younger women with unfulfilled reproductive potential, surgical treatment attempts to remove endometrial tissue and preserving the ovaries without damaging normal tissue.

In general, the diagnosis of endometriosis is confirmed during surgery, at which time ablative steps can be taken. Further steps depend on circumstances: a woman without infertility can be managed with hormonal medication that suppress the natural cycle and pain medication, while an infertile woman may be treated expectantly after surgery, with fertility medication, or with IVF. As to the surgical procedure, ablation (or fulguration) of endometriosis (burning and vaporizing the lesions with a pointy electric device) has shown high rate of short-term recurrence after the procedure. The best surgical procedure with much less rate of short-term recurrence is to excise (cut and remove) the lesions completely.

Conservative treatment consists of the destruction of the peritoneal disease, either by excision or ablation of the endometrium or adhesions (adhesiolysis), resection of endometriomas, excision of the endometrial cysts or endometriomas (endometriomata), called "cystectomy," and restoration of normal pelvic anatomy as much as is possible. Laparoscopy, besides being used for diagnosis, can also be used to perform surgery. It's considered a "minimally invasive" surgery because the surgeon makes very small openings (incisions) at (or around) the belly button and lower portion of the belly. A thin telescope-like instrument (the laparoscope) is placed into one incision, which allows the doctor to look for endometriosis using a small camera attached to the laparoscope. Small instruments are inserted through the incisions to remove the endometriosis tissue and adhesions. Because the incisions are very small, there will only be small scars on the skin after the procedure, and all endometriosis can be removed, and women recover from surgery quicker and have a lower risk of adhesions. 55% to 100% of women develop adhesions following pelvic surgery, which can result in infertility, chronic abdominal and pelvic pain, and difficult reoperative surgery.

Conservative treatment involves excision of endometriosis while preserving the ovaries and uterus, very important for women wishing to conceive, but may increase the risk of recurrence. Endometriosis recurrence following conservative surgery is estimated as 21.5% at 2 years and 40-50% at 5 years.

A hysterectomy (removal of the uterus) can be used to treat endometriosis in women who do not wish to conceive. However, this should only be done when combined with removal of the endometriosis by excision, as if endometriosis is not also removed at the time of hysterectomy, pain may still persist.

Most surgeons who perform 'last chance' or definitive surgery for endometriosis perform a hysterectomy and removal of both ovaries (to deliberately cause a surgical menopause—taking away the stimulation of the endometriosis that they have left behind). The problem with that is that the benefit of the ovarian hormones is lost, for bone and heart health, mood and libido, and the disease itself is left behind which can be symptomatic (e.g., deep disease). A different approach is to "cut out the bad and leave the good," which is to remove the uterus (if done childbearing, for the risk of adenomyosis), and all the disease (as best possible), so the patient can retain her ovaries and not be in menopause.

For women with extreme pain, a presacral neurectomy may be very rarely performed where the nerves to the uterus are cut. However, this technique is almost never used due to the high incidence of associated complications including presacral haematoma and irreversible problems with urination and constipation.

Progesterone counteracts estrogen and inhibits the growth of the endometrium. Such therapy (progesterone or progestins) can reduce or eliminate menstruation in a controlled and reversible fashion. Progestins are chemical variants of natural progesterone. An example of a Progestin is Dienogest (Visanne). Avoiding products with xenoestrogens, which have a similar effect to naturally produced estrogen and can increase growth of the endometrium.

Oral contraceptives reduce the menstrual pain associated with endometriosis. They may function by reducing or eliminating menstrual flow and providing estrogen support. Typically, it is a long-term approach. Recently Seasonale was FDA approved to reduce periods to 4 per year. Other OCPs have however been used like this off label for years.

Continuous hormonal contraception consists of the use of combined oral contraceptive pills without the use of placebo pills, or the use of NuvaRing or the contraceptive patch without the break week. This eliminates monthly bleeding episodes.

Danazol (Danocrine) and gestrinone are suppressive steroids with some androgenic activity. Both agents inhibit the growth of endometriosis but their use remains limited as they may cause hirsutism and voice changes.

Gonadotropin Releasing Hormone (GnRH) agonists work by increasing the levels of GnRH. Consistent stimulation of the GnRH receptors results in downregulation, inducing a profound hypoestrogenism by decreasing FSH and LH levels. While effective in some people, they induce unpleasant menopausal symptoms, and over time may lead to osteoporosis. To counteract such side effects some estrogen may have to be given back (add-back therapy). These drugs can only be used for six months at a time.

Lupron depo shot is a GnRH agonist and is used to lower the hormone levels in the woman's body to prevent or reduce growth of endometriosis. The injection is given in 2 different doses: a 3-month dose injection (11.25 mg); or a 6 month course of monthly injections, each with the dosage of 3.75 mg. Note that the symptoms will mostly come back after completing the Lupron courses. Long-term use of Lupron (over 5-6 months) is associated with severe side effects, and should not be offered to the women. Thus, Lupron is not considered a treatment option for endometriosis. Instead, it is widely used in the United States as the non-invasive method for the diagnosis of endometriosis.

Aromatase inhibitors are medications that block the formation of estrogen and have become of interest for researchers who are treating endometriosis.

Other useful medications include NSAIDs and other anti-inflammatories are commonly used in conjunction with other therapy. For more severe cases narcotic prescription drugs may be used. NSAID injections can be helpful for severe pain or if stomach pain prevents oral NSAID use. Also, opioids such as morphine sulphate tablets and other opioid painkillers work by mimicking the action of naturally occurring pain-reducing chemicals called "endorphins." There are different long acting and short acting medications that can be used alone or in combination to provide appropriate pain control.

III. Diagnosis of Endometriosis-Related Infertility

Antibodies may be generated against protein targets S1P receptors, or enzymes in the S21P synthetic pathway. Antibodies are defined by their binding specificity. Those of skill in the art are well aware of methods by which such antibodies can be made and identified. Assessing the binding specificity/affinity of a given antibody using techniques is also well known to those of skill in the art, thereby permitting one to determine what antibodies fall within the scope of this disclosure.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

A. Protein Detection Methods

In one aspect, the disclosure provides method for detection and quantitation of S1P, S1P receptors and S1P synthetic enzymes. A variety of different methodologies are available for the detection. In general, one can detect and quantitate proteins using antibodies that bind specifically or preferentially to this molecule, or one can employ HPLC and/or mass spectrometric methods for these purposes.

1. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) while newer quantitative methods are being developed using matrix assisted laser desorption/ionization (MALDI) followed by time of flight (TOF) MS. In accordance with the present invention, one can generate mass spectrometry profiles that are useful for analyzing protein expression of S1P receptors and S1P synthetic enzymes.

2. Immunodetection

In further embodiments, there are immunodetection methods for identifying and/or quantifying S1P, S1P receptors and S1P synthetic enzymes. Some immunodetection methods include enzyme linked immunosorbent assay (ELISA), radioimmunoassay (RIA), immunoradiometric assay, fluoroimmunoassay, chemiluminescent assay, bioluminescent assay, fluorescent activated cell sorting (FACS) and Western blot to mention a few. The steps of various useful immunodetection methods have been described in the scientific literature. In general, the immunobinding methods include obtaining a sample and contacting the sample with a first antibody in accordance with embodiments discussed herein, as the case may be, under conditions effective to allow the formation of immunocomplexes. It is also possible to perform in vivo assays.

Contacting the chosen biological sample with an antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to foci-related proteins. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Non-limiting examples of reporter molecules include enzymes, radiolabels, haptens, fluorescent labels, phosphorescent molecules, chemiluminescent molecules, chromophores, photoaffinity molecules, colored particles or ligands, such as biotin. The labels used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

i. ELISAs

Immunoassays are, in their most simple and direct sense, binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the foci is added to the wells. After binding and washing to remove non-specifically bound immune complexes, the bound antigen may be detected. Detection may be achieved by the addition of another anti-foci antibody that is linked to a detectable label. This type of ELISA is a simple "sandwich ELISA." Detection may also be achieved by the addition of a second anti-foci antibody, followed by the addition of a third antibody that has binding affinity for the second antibody, with the third antibody being linked to a detectable label.

In another exemplary ELISA, the samples suspected of containing the foci are immobilized onto the well surface and then contacted with anti-foci antibody. After binding and washing to remove non-specifically bound immune complexes, the bound anti-foci antibodies are detected. Where the initial anti-foci antibodies are linked to a detectable label, the immune complexes may be detected directly. Again, the immune complexes may be detected using a second antibody that has binding affinity for the first anti-foci antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

ii. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

iii. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art.

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

B. Nucleic Acid Detection

In another aspect, measuring expression of gene products comprises measuring RNA expression levels for any of the S1P-related proteins mentioned above. Measuring RNA expression levels may comprise performing RT-PCR, Northern blot or in situ hybridization.

Quantitative real-time PCR (qRT-PCR) may also be used to measure the differential expression of a plurality of biomarkers. In qRT-PCR, the RNA template is generally reverse transcribed into cDNA, which is then amplified via a PCR reaction. The amount of PCR product is followed cycle-by-cycle in real time, which allows for determination of the initial concentrations of mRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

A non-limiting example of a fluorescent reporter probe is a TaqMan® probe (Applied Biosystems, Foster City, Calif.). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction. To minimize errors and reduce any sample-to-sample variation, qRT-PCR may be performed using a reference standard. The ideal reference standard is expressed at a constant level among different tissues, and is unaffected by the experimental treatment. Suitable reference standards include, but are not limited to, mRNAs for the housekeeping genes glyceraldehyde-3-phosphate-dehydrogenase (GAPDH) and β-actin. The level of mRNA in the original sample or the fold change in expression of each biomarker may be determined using calculations well known in the art.

Luminex multiplexing microspheres may also be used to measure the differential expression of a plurality of biomarkers. These microscopic polystyrene beads are internally color-coded with fluorescent dyes, such that each bead has a unique spectral signature (of which there are up to 100).

Beads with the same signature are tagged with a specific oligonucleotide or specific antibody that will bind the target of interest (i.e., biomarker mRNA or protein, respectively). The target, in turn, is also tagged with a fluorescent reporter. Hence, there are two sources of color, one from the bead and the other from the reporter molecule on the target. The beads are then incubated with the sample containing the targets, of which up to 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of mRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an mRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple mRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

IV. Methods of Treatment

With respect to all methods described herein, reference to sphingosine kinase antagonist, S1P antagonist, S1P receptor agonist, and S1P receptor antagonist, also includes compositions comprising one or more of these agents. These compositions may further comprise suitable excipients, such as pharmaceutically acceptable excipients including buffers, which are well known in the art. The present disclosure can be used alone or in combination with other conventional methods of treatment.

A. Pharmaceutical Formulations and Routes of Delivery

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present invention comprise an effective amount of the S1P and S1P receptor inhibitors described elsewhere in this document, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, or topical. Alternatively, administration may be by intradermal, subcutaneous, intramuscular, intraperitoneal or intravenous injection. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present invention may be incorporated with excipients. The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present invention is the use of lipid delivery vehicles. Lipid vehicles encompass micelles, microemulsions, macroemulsions, liposomes, and similar carriers. The term micelle refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 μm.

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly (ethylene glycol)$_{2000}$) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio.

Exemplary amounts of lipid constituents used for the production of the liposome include, for instance, 0.3 to 1 mol or 0.4 to 0.6 mol of cholesterol; 0.01 to 0.2 mol or 0.02 to 0.1 mol of phosphatidylethanolamine; 0.0 to 0.4 mol or 0-0.15 mol of phosphatidic acid per 1 mol of phosphatidylcholine.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present invention, liposomes have a size of about 0.05 microns to about 0.5 microns, or having a size of about 0.05 to about 0.2 microns.

B. Antibody-Based Therapies

Anti-S1P antibodies have been developed as cancer treatments. The crystal structure of an anti-S1P monoclonal antibody bound with its ligand is provided as Protein Databank No. 319G. See also U.S. Serial No. 20070148168; U.S. Pat. Nos. 6,881,546 and 6,858,383; and U.S. Ser. No. 10/029,372, each of which are incorporated by reference in their entirety. SPHINGOMAB®, a murine monoclonal antibody (mAb) developed by Lpath, Inc. has been shown to be effective in treating cancer. A series of humanized anti-S1P monoclonal antibodies have been developed, and are described in U.S. Ser. Nos. 60/854,971 and 11/924,890, now issued as U.S. Pat. No. 7,829,674, and corresponding PCT application PCT/US2007/082647, each of which applications is incorporated by reference in its entirety. One particularly effective example of such a humanized antibody is referred to as LT1009 (available commercially as Sonepcizumab®, Lpath, Calif.), which antibody has exhibited greater activity than SPHINGOMAB® in the treatment of cancer.

In one aspect of the disclosure, anti-S1P antibodies and anti-S1P receptor antibodies are administered for reducing and blocking the biological activity of S1P. This antagonistic activity is believed to be useful in the treatment of endometriosis and endometriosis-related conditions such as infertility. Accordingly, in one aspect, the disclosure provides a method of antagonizing human S1P biological activity using any of the antagonists (including polypeptides and antibodies such as LT1009) disclosed herein. In one aspect, the method comprises contacting S1P with an antibody (including LT1009) described herein, whereby S1P activity is antagonized, reduced, blocked, or suppressed. In yet another aspect, an individual with endometriosis (such as an individual with endometriosis-related infertility) is treated with an anti-S1P antibody (including LT1009) or anti-S1P receptor antibody or combination thereof.

For simplicity, reference will be made generally to anti-S1P antibody (including LT1009) or anti-S1P receptor antibody with the understanding that these methods apply to any of the variant antibodies and polypeptides described herein.

Various formulations of anti-S1P antibody or anti-S1P receptor antibody or fragments (e.g., Fab, Fab', F(ab')2, Fv, Fc, etc.), such as single chain (ScFv), mutants thereof, fusion proteins comprising an antibody portion, and any other modified configuration of anti-S1P antibody or anti-S1P receptor antibody that comprises an S1P/S1P receptor (including $S1P_1$ receptor) recognition site of the required specificity, may be used for administration to an individual in need thereof. In some aspects, anti-S1P antibody and/or anti-S1P receptor antibody or various formulations thereof may be administered neat. In other aspects, anti-S1P antibody or anti-S1P receptor antibody or various formulations (including any composition aspect described herein) thereof and a pharmaceutically acceptable excipient can be administered, and may be in various formulations. Pharmaceutically acceptable excipients are known in the art. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and non-parenteral drug delivery are set forth in Remington, The Science and Practice of Pharmacy 20th Ed. Mack Publishing, 2000.

In some aspects, these agents are formulated for administration by injection (e.g., intraperitoneally, intravenously, subcutaneously, intramuscularly, etc.), although other forms of administration (e.g., oral, mucosal, via inhalation, sublingually, etc.) can be also used. Accordingly, anti-S1P antibody and/or anti-S1P receptor antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or less, is administered. For repeated administrations over several days or longer, depending on the condition, the treatment is sustained until a desired suppression of disease symptoms occurs. An exemplary dosing regimen comprises administering an initial dose of about 2 mg/kg, followed by a weekly maintenance dose of about 1 mg/kg of the anti-S1P antibody and/or anti-S1P receptor antibody, or followed by a maintenance dose of about 1 mg/kg every other week. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of symptoms to be treated, whether the agent is administered for preventive or therapeutic purposes, previous therapy, the patient's clinical history and response to the agent, and the discretion of the attending physician. Typically the clinician will administer an anti-S1P antibody and/or anti-S1P receptor antibody, until a dosage is reached that achieves the desired result. In some cases, sustained continuous release formulations of anti-S1P antibody and/or anti-S1P receptor antibody may be appropriate. Various formulations and devices for achieving sustained release are known in the art.

In one aspect, dosages for anti-S1P antibody and/or anti-S1P receptor antibody (or polypeptides) may be determined empirically in individuals who have been given one or more administration(s). Individuals are given incremental dosages of anti-S1P antibody and/or anti-S1P receptor antibody. To assess efficacy of anti-S1P antibody and anti-S1P receptor antibody or other equivalent antibody, symptoms of endometriosis/infertility can be monitored.

Administration of an anti-S1P antibody and/or anti-S1P receptor antibody in accordance with the methods of the present disclosure can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dosages.

Other formulations include suitable delivery forms known in the art including, but not limited to, carriers such as liposomes. See, for example, Mahato et al., 1997. Liposomal preparations include, but are not limited to, cytofectins, multilamellar vesicles and unilamellar vesicles.

In some aspects, more than one antibody may be administered. The antibodies can be monoclonal or polyclonal. Such compositions may contain at least one, at least two, at least three, at least four, at least five different antibodies. A mixture of antibodies, as they are often denoted in the art, may be particularly useful in treating a broader range of population of individuals.

The binding affinity of, for example, an anti-S1P antibody or anti-S1P receptor antibody for binding to S1P or S1P receptor, respectively, can be about 0.10 to about 0.80 nM, about 0.15 to about 0.75 nM and about 0.18 to about 0.72 nM. In one aspect, the binding affinity is between about 2 pM and 22 pM. In one aspect, the binding affinity is between about 23 pM and about 100 pM. In some aspects, the binding affinity is about 10 nM. In other aspects, the binding affinity is less than about 10 nM. In other aspects, the binding affinity is about 0.1 nM or about 0.07 nM. In other aspects, the binding affinity is less than about 0.1 nM or less than about 0.07 nM. In other aspects, the binding affinity is any of about 100 nM, about 50 nM, about 10 nM, about 1 nM, about 500 .mu.M, about 100 pM, or about 50 pM to any of about 2 pM, about 5 pM, about 10 pM, about 15 pM, about 20 pM, or about 40 pM. In some aspects, the binding affinity is any of about 100 nM, about 50 nM, about 10 nM, about 1 nM, about 500 pM, about 100 pM, or about 50 pM, or less than about 50 pM. In some aspects, the binding affinity is less than any of about 100 nM, about 50 nM, about 10 nM, about 1 nM, about 500 pM, about 100 pM, or about 50 pM. In still other aspects, the binding affinity is about 2 pM, about 5 pM, about 10 pM, about 15 pM, about 20 pM, about 40 pM, or greater than about 40 pM.

In some aspects of the present disclosure, the anti-S1P antibody binds human S1P, and does not significantly bind an S1P from another vertebrate species (in some aspect, mammalian). In some aspects, the antibody binds human S1P as well as one or more S1P from other vertebrate species (in some aspects, mammalian). In some aspects, the antibody binds to a mammalian species of S1P, such as horse or dog, but does not significantly bind to S1P from anther mammalian species. The same criteria of this paragraph can apply to other antibodies such as anti-S1P receptor antibodies.

The epitope(s) can be continuous or discontinuous. In one aspect, the antibody binds essentially the same S1P epitopes as described in U.S. Serial No. 20070148168; U.S. Pat. Nos. 6,881,546 and 6,858,383; U.S. Ser. No. 10/029,372; U.S. Ser. No. 60/854,971 and U.S. Ser. No. 11/924,890, and corresponding PCT application PCT/US2007/082647. It is understood that although the epitopes described above relate to mouse and human S1P, one of ordinary skill can align the structures of mouse and human S1P with the S1P of other species and identify likely counterparts to these epitopes.

If desired, the anti-S1P antibody or anti-S1P receptor antibody (monoclonal or polyclonal) of interest may be sequenced and the polynucleotide sequence may be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, if appropriate, the constant region may be engineered to mimic human constant regions to avoid immune response if the antibody is used in clinical trials and treatments in humans. It may be desirable to genetically manipulate the antibody sequence to obtain greater affinity to S1P and greater efficacy in inhibiting S1P. It will be apparent to one of skill in the art that one or more polynucleotide changes can be made to the anti-S1P antibody or anti-S1P receptor antibody and still maintain its binding affinity for S1P and S1P receptor, respectively.

Humanization of a monoclonal antibody can be achieved as follows: (1) determine the nucleotide and predicted amino acid sequence of the starting antibody light and heavy variable domains (2) design the humanized antibody, i.e., decide which antibody framework region to use during the humanizing process (3) apply humanizing methodologies/techniques and (4) transfection and expression of the humanized antibody. See, for example, U.S. Pat. Nos. 4,816, 567; 5,807,715; 5,866,692; 6,331,415; 5,530,101; 5,693, 761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al., 1991; Lobuglio et al., 1989; Shaw et al., 1987 and Brown et al., 1987. Other references describe rodent CDRs grafted into a human supporting framework region (FR) prior to fusion with an appropriate human antibody constant domain. See, for example, Riechmann et al., 1988; Verhoeyen et al., 1988 and Jones et al., 1986. Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g., PCT Publication No. PCT/GB99/01441; UK Patent Application No. 9809951.8. Other methods of humanizing antibodies that may also be utilized are disclosed by Daugherty et al., 1991 and in U.S. Pat. Nos. 6,180,377; 6,054,297; 5,997,867; 5,866,692; 6,210,671; and 6,350,861; and in PCT Publication No. WO 01/27160. LT1009 is an example of a humanized antibody.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Abgenix, Inc. (Fremont, Calif.) and HuMAb-Mouse® and TC Mouse® from Medarex, Inc. (Princeton, N.J.).

In an alternative, antibodies may be made recombinantly and expressed using any method known in the art. For example, antibodies may be made recombinantly by phage display technology. See, for example, U.S. Pat. Nos. 5,565, 332; 5,580,717; 5,733,743; and 6,265,150; and Winter et al., 1994. Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson and Chiswell, 1993. Several sources of V-gene segments can be used for phage display. Clackson et al., 1991 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., 1991 or Griffith et al., 1993. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., 1993. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody humanization of rodent antibodies by CDR grafting, this technique provides completely human antibodies, which have no framework or CDR residues of rodent origin.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al., 2001; Lonberg and Huszar, 1995 and Pollock, et al., 1999.

B. Non-Antibody Sphingosine Kinase Antagonists, S1P Antagonists and S1P Receptor Antagonists In one aspect, the disclosure provides methods that use a sphingosine kinase antagonist, S1P antagonist or S1P receptor antagonist, terms which refer to a non-antibody molecule that blocks, suppresses or reduces (including significantly) S1P biological activity, including downstream pathways mediated by S1P signaling, such as receptor binding and elicitation of a cellular response to S1P. The term "antagonist" implies no specific mechanism of biological action, and is deemed to expressly include and encompass all possible pharmacological, physiological, and biochemical interactions with S1P and its consequences which can be achieved by a variety of different, and chemically divergent, compositions.

Some known sphingosine kinase antagonists are agents which molecularly mimic the natural substrates of sphingosine kinase. Such antagonists bind to sphingosine kinase, in some instances irreversibly, and thereby prevent the binding of natural substrates of sphingosine kinase, ultimately preventing the phosphorylation of these substrates. Examples of sphingosine kinase antagonists include methylsphingosine, N,N-dimethyl sphingosine, trimethylsphingosine, D,L-threo-dihydrosphingosine and high density lipoprotein. Other sphingosine derivatives that can be used as sphingosine kinase inhibitors are described in U.S. Pat. Nos. 5,583,160; 5,627,171; 5,466,716; 5,391,800; 5,137,919; 5,151,360; 5,248,824; 5,260,288; and 5,331,014 (De Jonghe et al., 1999) disclose the use of short-chain sphingoid bases, including short chain sphinganine analogs and 3-fluoro-sphingosine analogs as inhibitors of sphingosine kinase. (De Jonghe et al., 1999).

Other sphingosine kinase antagonists may bind sphingosine kinase at sites other than the substrate binding site, provided they ultimately interfere with the catalytic activity of the kinase. A suitable sphingosine kinase antagonist may interfere with the catalytic activity of sphingosine kinase by interfering with or preventing the interaction with substrates or catalysts, or interfering or preventing the release of products, or by preventing the modification of the substrates by the enzyme. The cloning of murine sphingosine kinase (GenBank Accession Nos. AF068748, AF068749) has been reported by (Kohama et al., 1998) as have expression studies and activity studies aimed at measuring specific sphingosine kinase activity (Kohama et al., 1998). GenBank Accession Nos. NM021972 and XM012589 correspond to sequences of cloned human sphingosine kinase. Assays for any of the above agent classes have been described in the literature, and especially in PCT/AU98/00730 (WO 99/12533), which are incorporated herein by reference in their entirety, which documents methods for measuring sphingosine kinase activity as well as methods for identifying sphingosine kinase agonists and antagonists.

Exemplary S1P antagonists or S1P receptor antagonists include, but are not limited to an antisense or siRNA molecule directed to an S1PR or an enzyme in the S1P synthetic pathway, or an S1P structural analog. In some aspects of the disclosure, the sphingosine kinase antagonist, S1P antagonist or S1P receptor antagonist comprises at least one antisense molecule capable of blocking or decreasing the expression of at least one S1P activity. Nucleotide sequences of the sphingosine kinase and S1P receptors, including S1 P1, are known and are readily available from publicly available databases. It is routine to prepare antisense oligonucleotide molecules that will specifically bind sphingosine kinase or S1P receptor mRNA without cross-reacting with other polynucleotides. Exemplary sites of targeting include, but are not limited to, the initiation codon, the 5' regulatory regions, the coding sequence and the 3' untranslated region. In some aspects, the oligonucleotides are about 10 to 100 nucleotides in length, about 15 to 50 nucleotides in length, about 8 to 25 nucleotides in length, or more. The oligonucleotides can comprise backbone modifications such as, for example, phosphorothioate linkages, and 2'-O sugar modifications well know in the art.

Alternatively, S1P expression and release and S1P receptor expression can be decreased using gene knockdown, morpholino oligonucleotides, RNAi, or ribozymes, methods that are well-known in the art.

Targeted delivery of therapeutic compositions containing inhibitory nucleic acids can also be used. Receptor-mediated DNA delivery techniques are described in, for example, (Findeis et al., 1993; Chiou et al., 1994; Wu et al., 1988; Wu et al., 1994; Zenke et al., 1990; Wu et al., 1991). Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, 1994; Kimura, 1994; Connelly, 1995 and Kaplitt, 1994). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769, WO 93/19191, WO 94/28938, WO 95/11984 and WO 95/00655). Administration of DNA linked to killed adenovirus as described in (Curiel, 1992) can also be employed.

Non-viral delivery vehicles and methods can also be employed, including, but not limited to, polycationic condensed DNA linked or unlinked to killed adenovirus alone (see, e.g., Curiel, 1992) ligand-linked DNA (see, e.g., Wu, 1989); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in (Philip, 1994) and in (Woffendin, 1994).

In some aspects, an S1P inhibitory compound is a small molecule. A small molecule can have a molecular weight of about any of 100 to 20,000 daltons, 500 to 15,000 daltons, or 1000 to 10,000 daltons. Libraries of small molecules are commercially available. Small molecule inhibitors can be administered using any means known in the art, including inhalation, intraperitoneally, intravenously, intramuscularly, subcutaneously, intrathecally, intraventricularly, orally, enterally, parenterally, intranasally, or dermally. In general, when a sphingosine kinase antagonist, S1P antagonist, or S1P receptor antagonist according to the disclosure is a small molecule, it will be administered at a dose of 0.1 to 300 mg/kg of the weight of the patient divided into one to three or more doses. For an adult patient, doses ranging from 1 mg to 5 g per dose can be administered.

In other aspects, the sphingosine kinase antagonist, S1P antagonist, or S1P1 receptor antagonist comprises at least one S1P structural analog. "S1P structural analogs" in the present disclosure refer to compounds that have a 3-dimensional structure that is similar to at least a part of that of S1P and which bind to a sphingosine kinase or S1P receptor under physiological conditions in vitro or in vivo, wherein the binding of the analog at least partially inhibits an S1P biological activity, or S1P secondary messenger activity. In one aspect, the S1P structural analog binds to an S1P1 receptor. Suitable S1P structural analogs can be designed and synthesized through molecular modeling of S1P-receptor binding, for example by the method described in PCT Publication No. WO 98/06048.

Targeted delivery of therapeutic compositions containing an antisense polynucleotide, expression vector, or subgenomic polynucleotides can also be used according to the present disclosure. Receptor-mediated DNA delivery techniques are described in, for example, Findeis et al., 1993; Chiou et al., 1994; Wu et al., 1988; Wu et al., 1994; Zenke et al., 1990 and Wu et al., 1991. Therapeutic compositions containing a polynucleotide are administered in a range of about 100 ng to about 200 mg of DNA for local administration in a gene therapy protocol. In some aspects, concentration ranges of about 500 ng to about 50 mg, about 1 µg to about 2 mg, about 5 µg to about 500 µg, and about 20 µg to about 100 µg of DNA or more can also be used during a gene therapy protocol.

Example agonists include, but are not limited to, Fingolimod ("FTY720," trade name Gilenya®, Novartis Pharma AG, New York), BAF312 (Novartis Pharma AG, New York), Ponesimod (ACT-128800, Actelion Ltd., Switzerland), ONO-4641 (Ono Pharma, Japan), CS-0777 (Daiichi Sankyo, Japan), KRP-203 (Kyorin, Japan), PF-991 (Pfizer, New York), and W146 (Cayman Chemical, Michigan) (Brinkmann et al., 2010; Hla, et al., 2011; Cusack et al., 2010; Strader et al., 2011).

In aspects where the S1P receptor agonist is a small molecule, a small molecule can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. Usually, when the S1P receptor agonist according to the disclosure is a small molecule, it will be administered at the rate of 0.1 to 300 mg/kg of the weight of the patient divided into one to three or more doses. For an adult patient of normal weight, doses ranging from 1 mg to 5 g per dose can be administered.

V. Kits Comprising Agonists and Antagonists of the Disclosure

The disclosure also provides kits for both diagnostic and therapeutic purposes. The diagnostic kits will, in general, comprise antibodies that bind to S1P, S1 synthetic enzymes, and S1 receptors, and nucleic acid reagents that can hybridize to transcripts the encoding S1P synthetic enzymes and S1P receptors. Therapeutic kits may also contain sphingosine kinase antagonists, S1P antagonists, S1P receptor agonists, S1P receptor agonists and/or S1P receptor antagonists.

The kits may be used for any of the methods described herein, including, for example, to treat an individual with endometriosis (including endometriosis-related infertility). The kits may optionally provide additional components such as, buffers and instructions for use of any diagnostic to therapeutic agent in any of the methods described herein. In some aspects, the kits include instructions for treating endometriosis.

In other aspects, the kit comprises one or more of a sphingosine kinase antagonist, S1P antagonist, S1P agonist (such as Fingolimod, BAF312, Ponesimod, ONO-4641, CS-0777, KRP-203, PF-991, and W146), or S1P receptor antagonist (such as an anti-S1P antibody or $S1P_1$ receptor antibody) described herein and instructions for treating endometriosis in an individual.

In still further embodiments, there kits may be for use with immunodetection methods described above. The kits will thus comprise, in suitable container means, a first antibody that binds to Fuch's nuclear foci, and optionally an immunodetection reagent. The antibody may be pre-bound to a solid support, such as a column matrix and/or well of a microtitre plate. The antibodies may have detectable labels that are associated with or linked to the given antibody. Detectable labels that are associated with or attached to a secondary binding ligand are also contemplated. Exemplary secondary ligands are those secondary antibodies that have binding affinity for the first antibody.

The kits may further comprise a suitably aliquoted composition of a foci-related antigen, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the oligonucleotides, antibodies, and any other reagent containers in close confinement for commercial sale. Such containers may include injection or blow-molded plastic containers into which the desired vials are retained. Instructions may include variations that can be implemented.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

VI. Examples

The following examples are included to demonstrate certain non-limiting aspects of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1—Preliminary Data

FIG. 1 shows data produced from the inventor's feasibility study that indicates a trend towards a significant elevation in S1PR1 receptor levels in pain patients with endometriosis versus those without.

Example 2—Prophetic Example

Using proteomic analysis, the inventors will determine if the level of S1PR1 expression in peripheral blood leukocytes (PBLs) is increased in patients suffering from endometriosis with and without pain. To this end, leukocytes from heparinized blood will be separated from the plasma, and the erythrocytes lysed with 0.75% NH4Cl, 22 mM sodium bicarbonate, 2.5 pM EDTA for 5 min on ice. The leukocytes will be washed with 1×PBS and lysed in ice-cold homogenization buffer (Doyle et al., 2011a; 2011b). The level S1PR1 expression will be detected by immunoblot with rabbit anti-S1PR1 (1:1000, Abcam) and enhanced chemiluminescence detection, as previously described (Doyle et al., 2011a; 2011b). The bound peroxidase will be deactivated with 30% $H_2O_2$, as described (Veung et al., 2011) and the membranes then re-probed with mouse anti-actin (Sigma) as a loading control.

In order to provide standardized samples for comparison, a 3 mm punch biopsy will be used to create the peritoneal sample for lab analysis, with the rest of the peritoneum sent not. Only peritoneal samples that have enough tissue for both histological assessment (for endometriosis or not) and lab analysis will be used in the study. Peritoneal samples are stored frozen stored frozen at −800° C. until processed. The inventors will measure the mRNA levels of S1PR1 and the key SiP metabolic enzymes (SphK1, SphK2, SGPP1, SCPP2, SGPL1) [9] using two-step quantitative real-time Taq-Man RT-PCR (qRT-PCR, Qiagen). Biopsies will be preserved in RNALater® per manufacturer's instructions. The total RNA will be isolated and purified via the Chomczynski method [29] and spin-column RNA isolation kits (Qiagen). The relative changes in mRNA expression between patient groups will be measured using the comparative Ct method with HPRT1 as the endogenous control.

Levels of S1PR1 will be assessed between women with endometriosis and no pain (n=30), women with no endometriosis and pain (n=30), and women with both endometriosis and pain (n=120) with analysis of variance (ANOVA) or Kruskal-Wallis test depending on the normality of the distributions; pairwise comparisons will be made with independent students t-test or the Kolmogorov-Smirnov test depending on the normality of the distributions. The independent predictability of enzymes on severe pain (>7) will be assessed through multiple logistic regression. The ability of enzymes to discriminate between women with and without severe pain will be examined through Receiver Operating Characteristic (ROC) curve analysis. Similar predictability and discriminatory analyses will be performed with S1PR1 levels for severe pain in women with endometriosis and for endometriosis in women with severe pain.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

Aznaurova et al., Reprod Biol Endocrinol 12:50, 2014.
Ballard et al., Fertil Steril 94:20-27, 2010.
Boerner et al., J. Immunol., 147 (1):86-95, 1991.
Brinkmann et al., Nat. Rev. Drug Discov. 9, 883-897, 2010.
Brosens et al., Hum Reprod., 8:2026-2031, 2013.
Brown et al. Cancer Res. 47:3577-3583, 1987.
Bryant et al., Neurosci Lett 463:49-53, 2009.
Chiou et al., Gene Therapeutics: Methods And Applications Of Direct Gene Transfer (1. A. Wolff, ed.) 1994.
Chomczynski & Sacchi, Anal Biochem. 162:156-159, 1987.
Ciudice & Kao, Lancet 364:1789-1799, 2004.
Clackson et al., Nature 352:624-628, 1991.
Cole et al., Monoclonal Antibodies and Cancer Therapy, Alan R. Liss, p. 77, 1985.
Connelly, Human Gene Therapy, 1:185, 1995.
Curiel, Hum. Gene Ther., 3:147, 1992.
Cusack et al., Curr. Op. in Dr. Disc. and Dev. 13 (4): 481-488, 2010.
D'Hooghe et al., Gynecot Obstet. Invest. 62, 136-138, 2006.
Daugherty et al., Nucl. Acids Res. 19:2471-2476, 1991.
De Jonghe et al., Bioorg Med Chem Lett., 9 (21):3175-3180, 1999.
Delgadoww et al., Biochim Biophus Acta 1758:1957-1977, 2006.
Doyle et al., FASEB J. 25, 2782-2791, 2011a.
Doyle et al., Neurosci. Lett. 499, 4-8, 2011b.
EP Patent No. 0 345 242
EP Patent No. 0 519 596
EP Patent No. 0 524 968
Fassbender et al., Fertil Steril 99, 1135-1145, 2013.
Findeis et al., Trends Biotechnol., 11:202, 1993.
GB Patent No. 2,200,651
Griffith et al., EMBO J. 12:725-734, 1993.
Hadfield et al., Human Reproduction 11:878-880, 1996.
Hannun & Obeid, Nat. Rev. Mat Cell Blot 9, 139-150, 2008.
Hla et al., Neurology 2011, 76; 53, 2011.
Hoogenboom and Winter, J. Mol. Biol., 227:381, 1991.
Jacobson et al., Cochrane Database of Systematic Reviews 4, 2001.
Janes et al., J. Biol. Chem., 289(30):21082-97, 2014.
Jarrell et al., J Obstet Gynaecol Can 27, 869-910, 2005.
Johnson and Chiswell, Current Opinion in Structural Biology 3:564-571, 1993.
Jolly, Cancer Gene Therapy 1:51, 1994.
Jones et al., Nature 321:522-525, 1986.
Kaplitt, Nature Genetics 6:148, 1994.
Kennedy et al., Hum. Reprod. 20:2698-2704, 2005.
Kimura, Human Gene Therapy 5:845, 1994.
Kohama et al., J Biol Chem 273 (37):23722-8, 1998.
Lobuglio et al., Proc. Nat. Acad. Sci. USA 86:4220-4224, 1989.
Lonberg and Huszar, Int. Rev. Immunol. 13:65, 1995.
Mahato et al. Pharm. Res. 14:853-859, 1997.
Mark et al., J. Mol. Biol. 222:581-597, 1991.
Marks et al., Biotechnol. 10:779-783, 1992.
McCafferty et al., Nature 348:552-553, 1990.
Ndengele et al., J Pharmacol Exp Ther 329:64-75, 2009.
PCT Patent Application No. PCT/AU98/00730
PCT Publication No. PCT/GB99/01441
PCT Publication No. WO 01/27160
PCT Publication No. WO 98/06048
PCT Publication WO 90/07936
PCT Publication WO 90/11092
PCT Publication WO 91/02805
PCT Publication WO 91/14445
PCT Publication WO 93/03769
PCT Publication WO 93/10218
PCT Publication WO 93/11230
PCT Publication WO 93/19191
PCT Publication WO 93/25234
PCT Publication WO 93/25698
PCT Publication WO 94/03622
PCT Publication WO 94/12649
PCT Publication WO 94/23697
PCT Publication WO 94/28938
PCT Publication WO 95/00655
PCT Publication WO 95/07994
PCT Publication WO 95/11984
PCT Publication WO 95/13796
PCT Publication WO 95/30763
PCT Publication WO 96/17072
PCT Publication WO 97/42338
PCT Publication WO 99/12533
PCT/AU98/00730
PCT/US2007/082647
Peeters et al. Vaccine 19:2756, 2001.
Philip, Mol. Cell. Biol. 14:2411, 1994.
Pollock, et al., J Immunol Methods 231:147, 1999.
Remington's Pharmaceutical Sciences" 15th Edition, pages 1035-1038 and 1570-1580, 2000.
Riechmann et al., Nature 332:323-327, 1988.
Rosen & Goetzl, Nat. Rev. Immunot 5:560-570, 2005.
Rosen et al., Annu. Rev. Biochem. 78:743-768, 2009.
Rosen et al., Immunot Rev. 223:221-235, 2008.
Sabbadini, R. A., Br Pharmacol 162:1225-1238, 2011.
Salvemini et al., Trends Pharmacological sciences 34:110-118, 2013.
Santulli et al., FertilSteril 97:904-911, 2012.
Shaw et al., J. Immunol. 138:4534-4538, 1987.
Sheets et al., PNAS, (USA) 95:6157-6162, 1998.
Spiegel & Milstien, Nat. Rev. Immunat 11:403-415, 2011.
Strader et al., J. Nat. Prod. 74:900-907, 2011.

Stratton & Berkley, Hum Reprod Update 17:327-346, 2011.
Taha et al., Biochim Biophys Acta 1682:48-55, 2004.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,777,127
U.S. Pat. No. 4,816,567
U.S. Pat. No. 5,137,919
U.S. Pat. No. 5,151,360
U.S. Pat. No. 5,219,740
U.S. Pat. No. 5,248,824
U.S. Pat. No. 5,260,288
U.S. Pat. No. 5,331,014
U.S. Pat. No. 5,391,800
U.S. Pat. No. 5,422,120
U.S. Pat. No. 5,466,716
U.S. Pat. No. 5,530,101
U.S. Pat. No. 5,545,806
U.S. Pat. No. 5,545,807
U.S. Pat. No. 5,565,332
U.S. Pat. No. 5,569,825
U.S. Pat. No. 5,580,717
U.S. Pat. No. 5,580,859
U.S. Pat. No. 5,583,160
U.S. Pat. No. 5,585,089
U.S. Pat. No. 5,625,126
U.S. Pat. No. 5,627,171
U.S. Pat. No. 5,633,425
U.S. Pat. No. 5,661,016
U.S. Pat. No. 5,693,761
U.S. Pat. No. 5,693,762
U.S. Pat. No. 5,733,743
U.S. Pat. No. 5,750,373
U.S. Pat. No. 5,807,715
U.S. Pat. No. 5,814,482
U.S. Pat. No. 5,866,692
U.S. Pat. No. 5,997,867
U.S. Pat. No. 6,054,297
U.S. Pat. No. 6,180,370
U.S. Pat. No. 6,180,377
U.S. Pat. No. 6,210,671
U.S. Pat. No. 6,265,150
U.S. Pat. No. 6,331,415
U.S. Pat. No. 6,350,861
U.S. Pat. No. 6,747,014
U.S. Pat. No. 6,753,423
U.S. Pat. No. 6,858,383
U.S. Pat. No. 6,881,546
U.S. Pat. No. 7,172,879
U.S. Pat. No. 7,829,674
U.S. Pat. No. 7,829,674
UK Patent Application No. 9809951.8
Vaughan et al., 1996, Nature Biotechnology, 14:309-314.
Verhoeyen et al., Science 239:1534-1 536, 1988.
Veung et al., Fertility and Sterility 95:1909-1912, 2011.
Waterhouse et al., Nucl Acids Res 21:2265-2266, 1993.
Winter et al., Annu Rev. Immunol. 12:433-455, 1994.
Winter et al., Nature 349:293-299, 1991.
Woffendin, Proc. Natl. Acad. Set 91:1581, 1991.
Worley et al., International J Molecular Sci 14:5367-5379, 2013.
Wu et al., J. Biol. Chem. 263:621, 1988.
Wu et al., J. Biol. Chem. 266:338, 1991.
Wu et al., J. Biol. Chem. 269:542, 1994.
Wu, J. Biol. Chem. 264:16985, 1989.
Zenke et al., Proc. Natl. Acad. Sci. USA, 87:3655, 1990.

What is claimed is:

1. A method of treating endometriosis-related infertility in a subject comprising administering to said subject an inhibitor of SIP synthesis selected from the group consisting of Fingolimod, BAF312, Ponesimod, ONO-4641, CS-0777, KRP-203, PF-991, W146, and combinations thereof or an inhibitor of SIP-binding to an SIP receptor wherein the inhibitor of SIP-binding to the SIP receptor is LT1009.

2. The method of claim 1, wherein said inhibitor inhibits the expression or activity of at least one of SPHK1, SPHK2, SGPP1, SGPP2, SGPL1, SPHKAP, SIPR1, S1PR$_2$, S1PR$_3$, S1PR$_4$, and S1PR$_5$.

3. The method of claim 1, wherein said inhibitor inhibits binding of SIP to the SIP receptor.

4. The method of claim 1, wherein treating reduces one or more symptoms of endometriosis.

5. The method of claim 4, wherein said one or more symptoms are selected from the group consisting of pain, diarrhea, dysuria, constipation, chronic fatigue, nausea, vomiting, headaches, low-grade fevers, heavy and/or irregular periods, hypoglycemia or infertility.

6. The method of claim 1, wherein said subject is a human or non-human mammal.

7. The method of claim 1, wherein administering comprises oral, sublingual, transdermal, vaginal, intramuscular or subcutaneous injection.

8. The method of claim 7, wherein the oral administration is by pill or tablet, the transdermal administration is by patch, cream, gel or lotion, the vaginal administration is by suppository or gel, and systemic administration.

9. The method of claim 1, further comprising repeated administering of said inhibitor.

10. The method of claim 1, further comprising administering a second endometriosis-related infertility treatment to said subject.

11. The method of claim 10, wherein said second endometriosis-related infertility treatment is selected from hormonal therapy and/or surgical therapy.

* * * * *